United States Patent
Assefzadeh et al.

(10) Patent No.: US 10,222,468 B2
(45) Date of Patent: Mar. 5, 2019

(54) MINIATURIZED DIRECT DIGITAL-TO-IMPULSE RADAR SENSORS IN SILICON

(71) Applicant: WILLIAM MARSH RICE UNIVERSITY, Houston, TX (US)

(72) Inventors: M. Mahdi Assefzadeh, Houston, TX (US); Aydin Babakhani, Houston, TX (US)

(73) Assignee: William Marsh Rice University, Houston, TX (US)

( * ) Notice: Subject to any disclaimer, the term of this patent is extended or adjusted under 35 U.S.C. 154(b) by 461 days.

(21) Appl. No.: 15/021,978

(22) PCT Filed: Sep. 29, 2014

(86) PCT No.: PCT/US2014/058019
§ 371 (c)(1),
(2) Date: Mar. 15, 2016

(87) PCT Pub. No.: WO2015/105546
PCT Pub. Date: Jul. 16, 2015

(65) Prior Publication Data
US 2016/0223669 A1  Aug. 4, 2016

Related U.S. Application Data

(60) Provisional application No. 61/883,305, filed on Sep. 27, 2013.

(51) Int. Cl.
*G01S 13/89* (2006.01)
*G01S 7/03* (2006.01)
(Continued)

(52) U.S. Cl.
CPC .......... *G01S 13/89* (2013.01); *E21B 47/0002* (2013.01); *E21B 47/122* (2013.01);
(Continued)

(58) Field of Classification Search
CPC ..... G01V 3/30; E21B 47/0002; E21B 47/122; G01N 22/00; G01S 13/0209; G01S 13/89;
(Continued)

(56) References Cited

U.S. PATENT DOCUMENTS

| 4,814,768 A | 3/1989 | Chang |
| 5,552,786 A | 9/1996 | Xia et al. |

(Continued)

OTHER PUBLICATIONS

L. J. Bond, et. al., "Evaluation of Non-Nuclear Techniques for Well Logging: Technology Evaluation", U.S. Department of Energy, PNNL-19867, Nov. 2010.
(Continued)

*Primary Examiner* — Timothy X Pham
(74) *Attorney, Agent, or Firm* — Winstead PC

(57) ABSTRACT

A radar system may comprise a trigger, driver, switching circuit, and antenna for generating an ultra-short impulse without utilizing an oscillator. A radar imaging system for imaging a formation or a cross section of a pipeline may include at least one radar sensor. The system may transmit a high-frequency, short impulse signal to a formation or pipeline and measure a reflected signal. A high speed impulse generator may allow the short impulse signals to be generated. This impulse generator may utilize a switching circuit and digital driver to provide the short impulse signals. The images provide useful information about complex permittivity of the formation, the geometry of the pipeline, deposition thickness of asphaltenes and wax, velocity of the fluid, as well as size, type, concentration of gas bubbles, water, or solid particles in the flow, or combinations thereof.

19 Claims, 22 Drawing Sheets

(51) Int. Cl.
| | |
|---|---|
| *G01S 7/282* | (2006.01) |
| *G01S 13/02* | (2006.01) |
| *G01V 3/30* | (2006.01) |
| *G01N 22/00* | (2006.01) |
| *H01Q 1/38* | (2006.01) |
| *E21B 47/00* | (2012.01) |
| *E21B 47/12* | (2012.01) |
| *G01S 7/41* | (2006.01) |

(52) U.S. Cl.
CPC .............. *G01N 22/00* (2013.01); *G01S 7/032* (2013.01); *G01S 7/038* (2013.01); *G01S 7/282* (2013.01); *G01S 7/411* (2013.01); *G01S 13/0209* (2013.01); *G01V 3/30* (2013.01); *H01Q 1/38* (2013.01)

(58) Field of Classification Search
CPC .......... G01S 7/032; G01S 7/038; G01S 7/282; G01S 7/411; H01Q 1/38
See application file for complete search history.

(56) References Cited

U.S. PATENT DOCUMENTS

| | | | |
|---|---|---|---|
| 6,191,724 | B1 | 2/2001 | McEwan |
| 7,420,503 | B2 | 9/2008 | Uchino |
| 7,781,737 | B2 | 8/2010 | Zhdaneev |
| 7,830,989 | B2 | 11/2010 | Mohamadi |
| 2006/0039449 | A1 | 2/2006 | Fontana et al. |
| 2007/0293174 | A1* | 12/2007 | Hayden ................... G01S 7/292 455/214 |
| 2008/0062036 | A1 | 3/2008 | Funk et al. |
| 2008/0304560 | A1* | 12/2008 | Aoyagi ................... G01S 7/006 375/239 |
| 2010/0066585 | A1 | 3/2010 | Hibbard et al. |
| 2013/0154846 | A1 | 6/2013 | Mangione et al. |
| 2014/0024941 | A1* | 1/2014 | Umeda .................... A61B 8/14 600/445 |
| 2014/0168004 | A1* | 6/2014 | Chen ........................ G01S 7/282 342/118 |
| 2016/0218725 | A1* | 7/2016 | Stoner .................... H03L 7/0812 |

OTHER PUBLICATIONS

A. Babakhani, D. B. Rutledge, and A. Hajimiri, "Transmitter Architectures Based on Near-Field Direct Antenna Modulation (NFDAM)," in IEEE J. Solid-State Circuits, vol. 43, No. 12, pp. 2674-2692, Dec. 2008.
A. Babakhani, X. Guan, A. Komijani, A. Natarajan, and A. Hajimiri, "A 77 GHz Phased Array Transceiver with On-Chip Dipole Antennas: Receiver and Antennas," in IEEE J. Solid-State Circuits, vol. 41, No. 12, pp. 2795-2806, Dec. 2006.
A. Natarajan, A. Komijani, X. Guan, A. Babakhani, and A. Hajimiri, "A 77 GHz Phased Array Transceiver with On-Chip Dipole Antennas: Transmitter and Local LO-Path Phase Shifting," in IEEE J. Solid-State Circuits, vol. 41, No. 12, pp. 2807-2819, Dec. 2006.
S. Jeon, Y. Wang, H. Wang, F. Bohn, A. Natarajan, A. Babakhani, and A. Hajimiri, "A Scalable 6-to-18 GHz Concurrent Dual-Band Quad-Beam Phased-Array Receiver in CMOS," in IEEE J. Solid-State Circuits, pp. 2660-2673, Dec. 2008.
J. Buckwalter, A. Babakhani, A. Komijani, and A. Hajimiri, "An Integrated Subharmonic Coupled-Oscillator Scheme for a 60-GHz Phased-Array Transmitter," in IEEE Transactions on Microwave Theory and Techniques, vol. 54, No. 12, pp. 4271-4280, Dec. 2006.
A. Hassibi, A. Babakhani, and A. Hajimiri, "A Spectral-Scanning Nuclear Magnetic Resonance Imaging (MRI) Integrated Transceiver," in IEEE J. Solid-State Circuits, vol. 44, No. 6, pp. 1805-1813, Jun. 2009.
T. Chen, et. al., "On the High-Temperature (to 300 C) Characteristics of SiGe HBTs," in IEEE Transactions on Electron Devices, vol. 51, No. 11, pp. 1825-1832, Nov. 2004.
X. Yang, P. Seifi, and A. Babakhani, "A Single-Chip Dual-Mode CW/Pulse Electron Paramagnetic Resonance Spectrometer in 0.13μm SiGe BiCMOS," in IEEE MTT-S Int. Microwave Symposium, Jun. 2013.
C. Chen, P. Seifi, and A. Babakhani, "A Silicon-Based, Fully Integrated Pulse Electron Paramagnetic Resonance System for mm-Wave Spectroscopy," in IEEE MTT-S Int. Microwave Symposium, Jun. 2013.
A. Babakhani, D. Liu, M. Sanduleanu, and S. Reynolds, "A Near-field Millimeter-wave Dielectric Imaging Technique with Sub-wavelength Spatial Resolution", Infrared, Millimeter and Terahertz Waves (IRMMW-THz), 2011 36th International Conference on, Houston, TX, 2011, pp. 1-2.
R. Han, and E. Afshari, "A 260GHz broadband source with 1.1 mW continuous-wave radiated power and EIRP of 157dBm in 65nm CMOS," Solid-State Circuits Conference Digest of Technical Papers (ISSCC), 2013 IEEE International, pp. 138, 139,17-21, Feb. 2013.
A. Arbabian, et al., "A 94 GHz mm-Wave-to-Baseband Pulsed-Radar Transceiver with Application in Imaging and Gesture Recognition," Solid-State Circuits, IEEE Journal of, vol. 48, No. 4, pp. 1055,1071, Apr. 2013.
K. Sengupta, and A. Hajimiri, "A 0.28 THz Power-Generation and Beam-Steering Array in CMOS Based on Distributed Active Radiators," Solid-State Circuits, IEEE Journal of, vol. 47, No. 12, pp. 3013, 3031, Dec. 2012.
Cheng, P. Hallbjorner, and A. Rydberg, "Printed Slot Planar Inverted Cone Antenna for Ultrawideband Applications," Antennas and Wireless Propagation Letters, IEEE, vol. 7, pp. 18,21, 2008.

\* cited by examiner

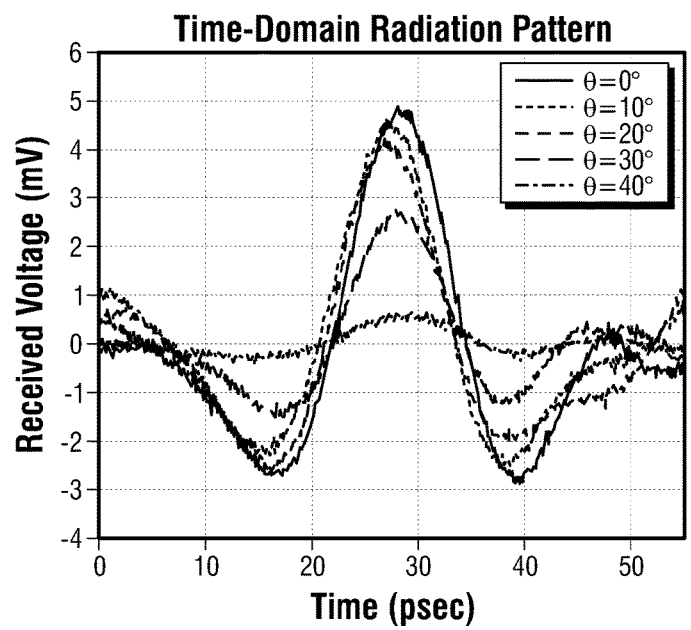
FIG. 10A
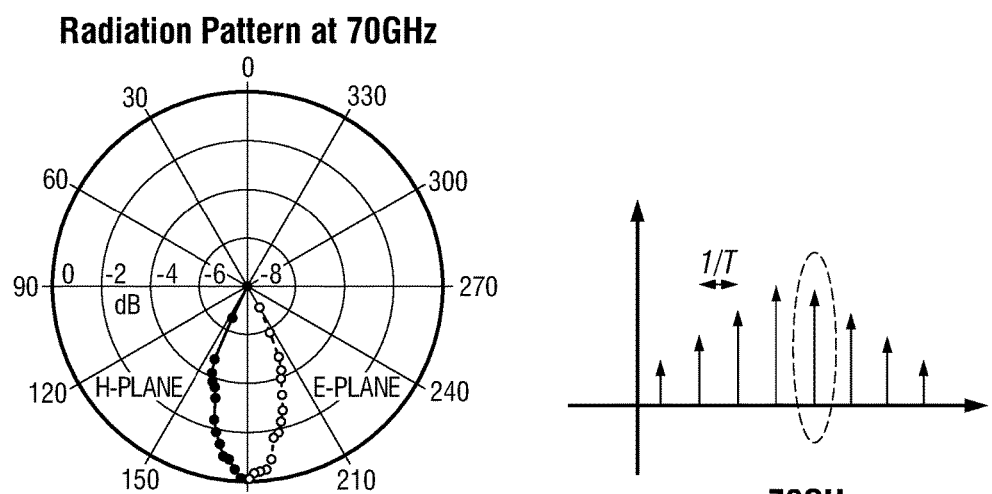
FIG. 10B
FIG. 10C

| PARAMETER | THIS WORK | [1] ISSCC 2013 | [2] JSSC 2013 | [3] VLSI 2013 |
|---|---|---|---|---|
| SHORTEST RADIATED PULSE (psec) | 8 (50%-50%) | 45 | 26 (50%-50%) | 100 |
| PEAK EIRP (dBm) | 13 | 15.7 | 13 | 14.5 |
| PHASE SYNCHRONIZATION WITH AN EXTERNAL REFERENCE | YES | NO | YES | NO |
| TIME-DOMAIN MEASUREMENTS | YES (WITH LOCKING) | NO | YES (W/O LOCKING) | NO |
| PULSE GENERATION METHOD | DIGITAL-TO-IMPULSE | OSCILLATOR-BASED | OSCILLATOR-BASED | OSCILLATOR-BASED |
| POWER CONSUMPTION (mW) | 220 (10GHz REP.) | 800 | 580 (TX+RX) | 1400 |
| TECHNOLOGY | 0.13μm SiGe BiCMOS | 65nm CMOS | 0.13μm SiGe BiCMOS | 65nm CMOS |
| DIE AREA (mm$^2$) | 0.47 | 2.25 | 6.16 | 20 |

*FIG. 13*

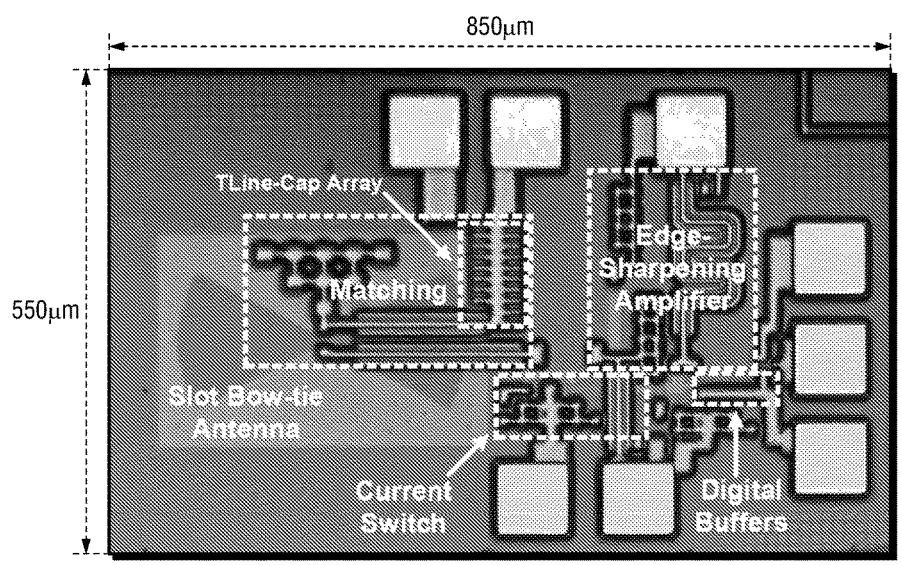

*FIG. 14*

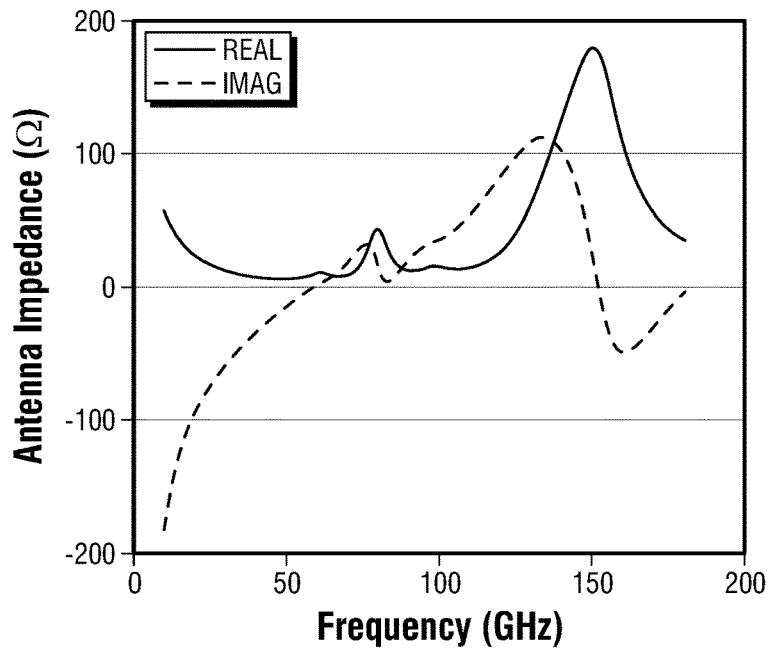
*FIG. 20*
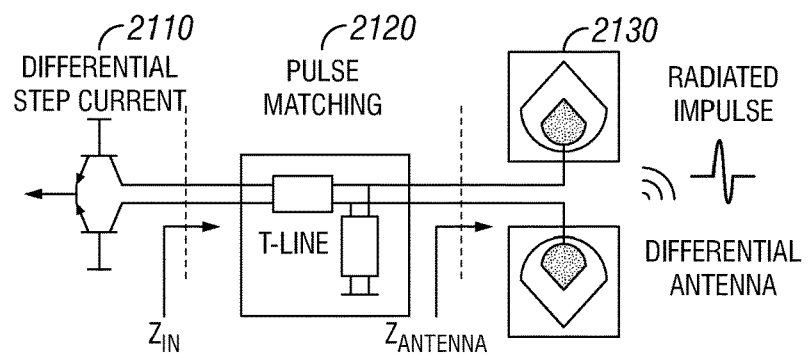
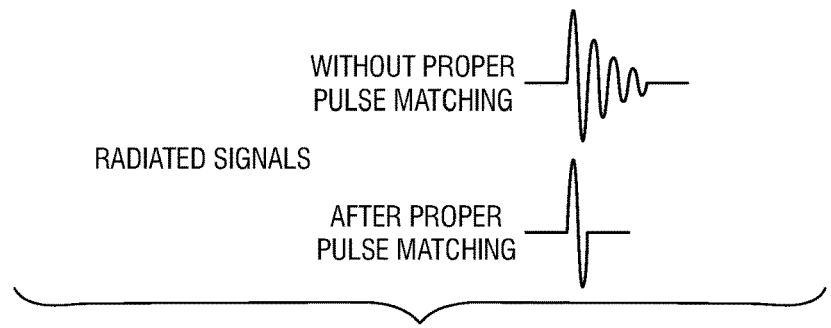
*FIG. 21*

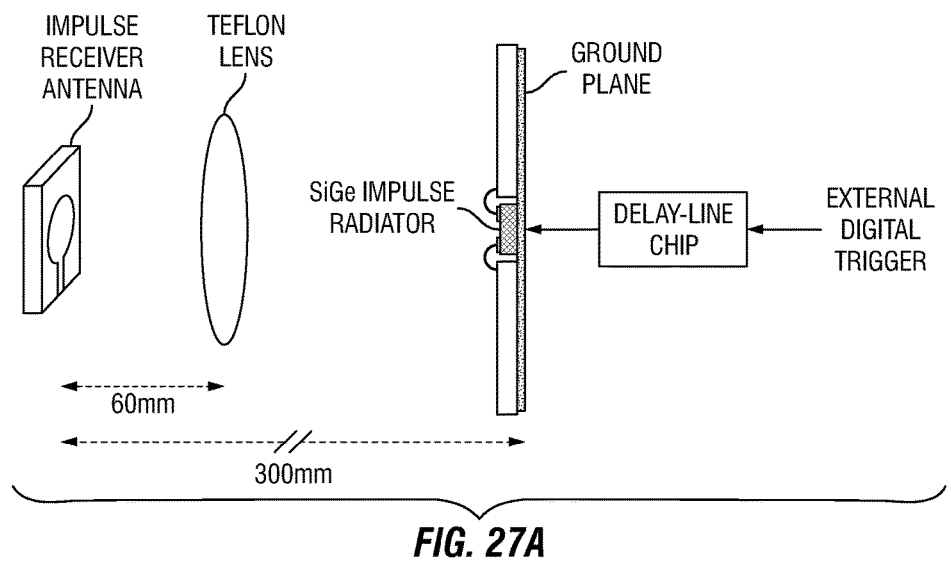
FIG. 27A
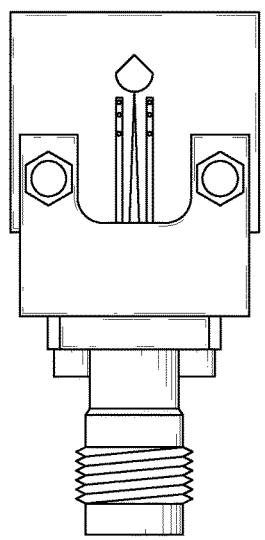 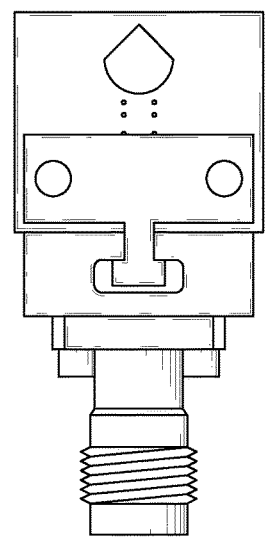
FIG. 27B   FIG. 27C

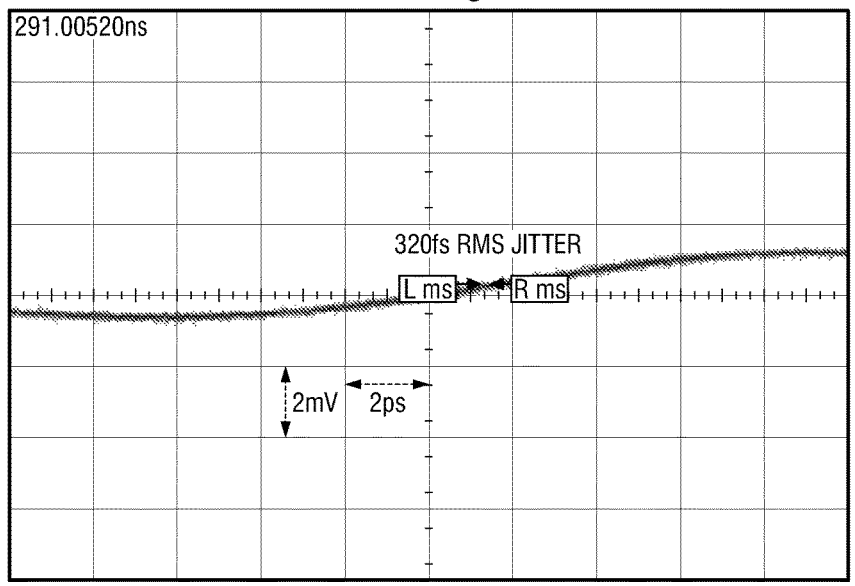

FIG. 30C

| PARAMETER | THIS WORK | [1] ISSCC 2013 | [2] JSSC 2013 | [3] VLSI 2013 |
|---|---|---|---|---|
| SHORTEST RADIATED PULSE (psec) | 9 (50%-50%) | 45 | 26 (50%-50%) | 100 |
| PEAK EIRP (dBm) | 10 | 15.7 | 13 | 14.5 |
| PHASE SYNCHRONIZATION WITH AN EXTERNAL REFERENCE | YES | NO | YES | NO |
| TIME-DOMAIN MEASUREMENTS | YES (WITH LOCKING) | NO | YES (W/O LOCKING) | NO |
| PULSE GENERATION METHOD | DIGITAL-TO-IMPULSE | OSCILLATOR-BASED | OSCILLATOR-BASED | OSCILLATOR-BASED |
| POWER CONSUMPTION (mW) | 260 (10GHz REP.) | 800 | 580 (TX+RX) | 1400 |
| TECHNOLOGY | 0.13μm SiGe BiCMOS | 65nm CMOS | 0.13μm SiGe BiCMOS | 65nm CMOS |
| DIE AREA (mm²) | 0.88 | 2.25 | 6.16 | 20 |

FIG. 31

MINIATURIZED DIRECT DIGITAL-TO-IMPULSE RADAR SENSORS IN SILICON

CROSS-REFERENCE TO RELATED APPLICATIONS

This application claims priority to U.S. Provisional Patent Application No. 61/883,305, filed on Sep. 27, 2013. The entirety of the aforementioned application is incorporated herein by reference.

STATEMENT REGARDING FEDERALLY SPONSORED RESEARCH

This invention was made with government support under Grant No. YFA-N66001-12-1-4214 awarded by the United States Department of Defense. The government has certain rights in the invention.

FIELD OF THE INVENTION

This invention relates to direct digital-to-impulse high-resolution radar imaging systems and methods.

BACKGROUND OF INVENTION

There is a considerable interest in radiating ultra-short broadband pulses in mm-wave and THz regime for applications in 3D imaging, spectroscopy, ranging, chemical sensing, precision time transfer, precision frequency transfer, and high-speed wireless communication that may have applicability to a wide variety of technology areas, such as oil and gas, medical, gaming, etc. Unfortunately, the pulse width of the prior silicon-based radiators is not short enough and their bandwidth is limited.

The oil and gas industry uses various logging tools to measure formation properties such as porosity, fluid saturation, fluid type, and permeability. Furthermore, they are used for geo-steering in horizontal drilling and fracture detection. The sensors should provide high vertical and azimuth resolutions. FIG. 1 summarizes the performance of existing logging tools. Although conventional high-resolution tools such as micro-resistivity sensor provide resolution of few cm, they are not suitable for operation with oil-based mud. The resistivity measurement requires passing electric current through a conductive borehole fluid, which cannot be done with oil-based mud. By increasing the frequency, it is possible to perform capacitive logging. Although capacitive probing is possible in oil-based mud, it is very difficult to calibrate the tool and measure the complex permittivity of the formation with high accuracy. A capacitive probe measures the combined permittivity of the mud, mudcake, and the actual formation. Since the permittivity and thickness of mud and mud-cake vary, a precise calibration becomes very challenging.

A radar imaging system and method discussed herein may provide high-resolution imaging. The system may provide solid-state impulse radar sensors in the frequency range from 1 GHz to 1 THz. The radar sensor may radiate ultra-short impulses with duration of 50 psec or less to the formation and measure the reflected signal. Further, the radar sensor does not require a continuous wave oscillator to provide narrow pulses. The radiated pulse can penetrate through the high-resistivity oil-based mud and image the formation behind the mud. Since the radar sensor is not a contact-based probe, it can provide high-resolution images in nonconductive oil-based mud. The radar sensor may provide vertical resolution of 10 mm or better, azimuth resolution of 5° or better, and investigation depth of 10 cm or better.

The radar sensor can also be used to image the cross section of oil pipelines. The pipeline images provide useful information about the geometry of the pipeline, deposition thickness of asphaltenes and wax, velocity of the fluid, as well as size, type, and concentration of gas bubbles, water, or solid particles in the flow.

SUMMARY OF THE INVENTION

In one embodiment, a radar imaging system for imaging may include at least one radar sensor. The system may transmit a high-frequency, short impulse signal to an area of interest and measure a reflected signal. In some embodiments, a frequency range of the impulse signal may be equal to or between 1 GHz to 1 THz. In some embodiments, the impulse signal may have a duration of 50 psec or less. In some embodiments, the impulse signal may have a duration of 10 psec or less. A high speed impulse generator may allow the short impulse signals to be generated. This impulse generator may utilize a switching circuit and digital driver to provide the short impulse signals.

In one embodiment, a radar imaging system for imaging a formation may include at least one radar sensor. The system may transmit a high-frequency, short impulse signal to a formation and measure a reflected signal. In some embodiments, a frequency range of the impulse signal may be equal to or between 1 GHz to 1 THz. In some embodiments, the impulse signal may have a duration of 50 psec or less. In some embodiments, the impulse signal may have a duration of 10 psec or less. A high speed impulse generator may allow the short impulse signals to be generated. This impulse generator may utilize a switching circuit and digital driver to provide the short impulse signals.

In another embodiment, a radar sensor can also be used to image the cross section of pipelines during production. The pipeline images provide useful information about the geometry of the pipeline, deposition thickness of asphaltenes and wax, velocity of the fluid, as well as size, type, concentration of gas bubbles, water, or solid particles in the flow, or combinations thereof.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIGS. 10A-10C show time-domain radiation pattern, radiation pattern at 70 GHz, and the frequency-domain EIRP of the impulse radiating;

FIG. 13 shows a comparison of the specifications of the chip discussed herein with the other chips;

FIG. 14 shows a micrograph of the chip;

FIG. 20 shows the real and imaginary impedance of the differential inverted-cone on-chip antenna;

FIG. 21 shows the architecture of the differential impulse radiator;

FIGS. 27A-27C are an illustrative embodiment of a measurement setup and photographs of the front and back of the designed impulse receiver antenna;

FIGS. 30A-30C show the delayed timing of the radiated impulse in the air by 150-fs, a graphical illustration of jitter and delaying of the signal, and the jitter of the radiated signals; and FIG. 31 shows a comparison of the specifications of the differential impulse radiator discussed herein with the other chips.

DETAILED DESCRIPTION

Figure 1:
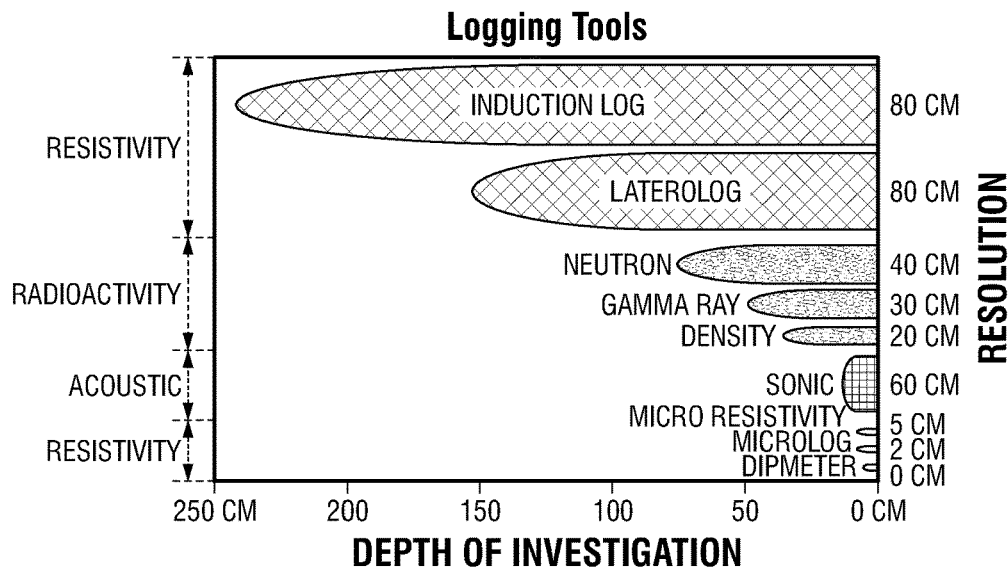
FIG. 1 shows the performance of existing logging tools.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

Systems and methods utilizing an ultra-short radar sensor. The systems and methods may utilize radar sensors for high-resolution imaging. In some embodiments, the system and methods for imaging discussed herein may be utilized to aid formation logging, flow assurance or the like. While the following discussion focuses on imaging, the radar systems and methods may also be suitable for other applications, including, but not limited to, ranging, spectroscopy, chemical sensing, precision time transfer, precision frequency transfer, and/or high-speed impulse communication. In some embodiments, a radar sensor may comprise a trigger, driver, switching circuit, and antenna for generating an impulse without utilizing an oscillator. In some embodiments, the system may be capable of imaging the formation with vertical resolution of 10 mm or better. In some embodiments, the system may be capable of imaging the formation with vertical resolution of 1 mm or better. In some embodiments, the system may utilize wide-band impulse radar sensors. In some embodiments, the radar sensors may radiate ultra-short time-domain impulses to a formation and measure the reflected signal. In some embodiments, ultra-short time-domain impulses may be 100 psec or less. In some embodiments, ultra-short time-domain impulses may be 50 psec or less. In some embodiments, ultra-short time-domain impulses may be 10 psec or less. In some embodiments, ultra-short time-domain impulses can be as small as 1 psec. The reflected signal from different boundaries will arrive in different times at the receiver. Due to the separation in time and using minimal calibration, measurement detected by the receiver may be used to determine complex permittivity of the formation without being affected by the mud properties. While the exemplary embodiments discussed herein discuss radar imaging of formations for well logging and pipelines for flow assurance, the radar imaging systems and methods discussed herein have broad applicability to various circumstances where imaging is desired. It will be recognized by one of ordinary skill that these radar imaging systems and methods are not limited to well logging, flow assurance, or oilfield applications. The radar imaging systems and methods discussed herein may be utilized in a variety of applications—nonlimiting examples may include well logging, flow assurance, oilfield applications, medical applications, gaming applications (gaming consoles), ranging, spectroscopy, chemical sensing, precision time transfer, precision frequency transfer, high-speed impulse communication, etc. As a nonlimiting example, the radar sensor can be used as a part of gaming console to capture 3D images of a player. As a nonlimiting example, the radar sensor can be used in a collision avoidance radar system for automotive, planes, unmanned aerial vehicles (UAVs), or the like.

In some embodiments, the impulse radiating radar sensor can be used to transfer time over a line-of-sight wireless link with accuracy of better than 100 fsec. The impulse radiating radar sensor can be used to transfer frequency over a line-of-sight wireless link in frequencies between 1 GHz and 1 THz with accuracy of better than 50 parts in 1000 billions (0.05 ppb).

It is important to note that for every vertical position and azimuth angle, a time-domain signal can be measured. The signal contains information on the frequency dependent reflectivity of the formation at different depths of investigation. For example, in some embodiments, signals may be produced at various depths in a desired frequency range. A reflected signal from the formation is detected, and the reflected signal may be analyzed to determine the different materials that are present in the formation. By determining a time-domain waveform of the reflect signal, the material and electrical permittivity of a material may be determined. In some embodiments, the materials may exhibit different reflection signals or attenuation in certain frequency ranges. In contrast with conventional resistivity logging tools, which provide only 2 dimensions of information, the data captured by the radar sensor has 5 dimensions of information: vertical position, azimuth angle, depth of investigation, frequency spectrum, and polarization. These 5 dimensions of information allow location and the type of different materials in the formation to be determined. The vertical and azimuth resolution of the proposed sensor is determined by the highest frequency component used in the time-domain impulse. The frequency spectrum of the reflected pulse can be used to extract the reflection properties of the formation as a function of frequency, thereby allowing the material and electrical permittivity of the material to be determined. This information is essential in identifying the type and porosity of the materials (in a flow or in a formation). The information gathered from the reflected signal can be used to determine the size or existence of the fractures. The radar systems and methods discussed herein can be utilized to determine the type of the rock, oil, water, gas, shale, or the like present in a formation, well, or pipeline.

Polarization is a key parameter in logging. Since reservoirs have layered structures, their reflection properties are a strong function of the polarization of the incident electromagnetic waves. This is extremely helpful in reducing the measurement errors caused by mud and mud-cake. Due to the fact that the formation is not an isotropic dielectric, but the mud and mud cake are, the imaging system may measure two orthogonal polarizations to generate polarization images that only depend on the formation properties. The polarization information can be used to sense the properties of the formation without begin severely affected by the mud and mud-cake.

Logging systems, such as U.S. Pat. Nos. 4,814,768 and 5,552,786, which are incorporated by reference, utilize low frequency (MHz) radar. The systems and methods discussed herein operate at high frequencies. In some embodiments, high frequency may be considered to be frequencies that are equal to or higher than 1 GHz. In some embodiments, high frequency may be considered to be frequencies that are equal to or between 1 GHz and 100 GHz. In one embodiment, the system may operate at frequencies that are equal to or between 1 GHz to 1 THz. In some embodiments, the radar beam can be focused into a spot size equal to or less than 10 mm. In the mm-wave (30-300 GHz) and THz (300 GHz-3 THz) frequency range, the radar beam can be focused into a spot size equal to or smaller than 1 mm. In some embodiments, beam focusing can be provided by utilizing an antenna array or a focusing lens. The depth of investigation of the sensor may be determined by the lowest frequency component of the impulse and the dynamic range of the radar transceiver. This is because the low-frequency waves can penetrate deeper into the formation due to the low level of the absorption.

Due to the high dynamic range of a radar transceiver, the sensor can be used in high signal loss situations. For example, the proposed 100 GHz sensor can radiate impulses with peak power of 100 mW (20 dBm), and the radar receiver can detect signals as weak as $10^{-7}$ mW (−70 dBm). This means that the sensor can operate with attenuation level as high as 90 dB. In other words, the reflected signal can be 90 dB ($10^{-9}$ times) weaker than the transmitted signal.

The length of the pulse in the propagating medium determines the depth resolution in 3D images. For example, the length of a 10 psec impulse is 3 mm in air and 1.0 mm in a medium with dielectric constant of 9.

One of the challenges of the radar system is blocking the direct coupling from the transmitter to the receiver. If transmitter and receiver operate at the same time, the output of the transmitter may couple to the input of the receiver. This high level of coupling can easily saturate the receiver and prevent it from detecting weak signals of the formation. To alleviate this problem, an active cancellation scheme can be used. In this scheme, an attenuated copy of the transmitted signal can be phase-shifted and added at the receiver to cancel the effects of near-field coupling between the transmitter and the receiver.

Figure 2A:
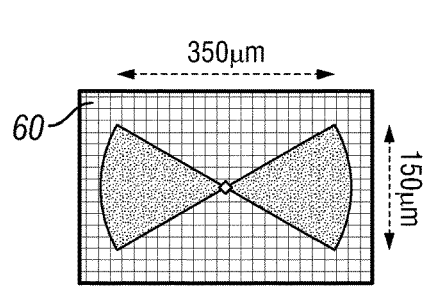
FIGS. 2A-2D are illustrative embodiments of a broadband on-chip antenna with its feed including (a) a close-up view of a bow-tie shaped slot antenna, (b) a view of the antenna on a substrate and lens, (c) a close-up view of the bow-tie shaped slot antenna with DC biasing pads and transmission lines, and (d) another view of the antenna on a substrate and lens.
Figure 2B:
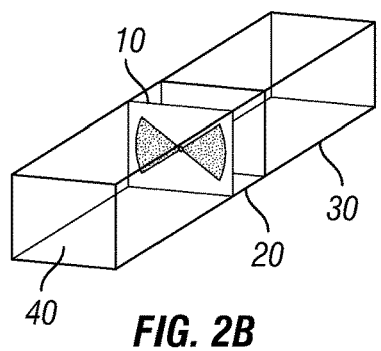
Figure 2C:
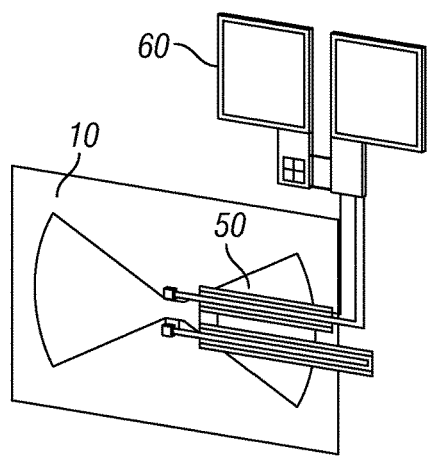
Figure 2D:
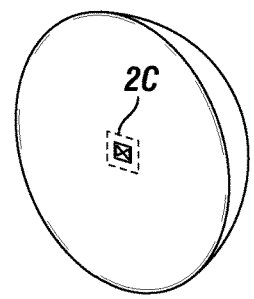
Figure 3:
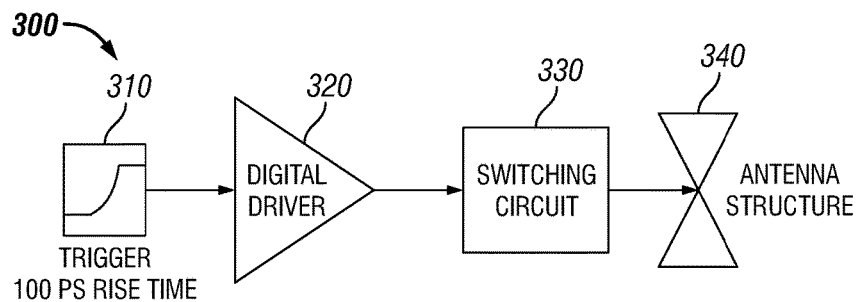
FIG. 3 is an illustrative embodiment of a block diagram of a picosecond pulse radiator.

An illustrative embodiment of impulse generation technique that can turn on or off the transmitter in 10 psec or less is discussed herein. In some embodiments, a transmitter may be capable of generating a signal with pulse-widths of 5 ps or less and a central frequency of 110 GHz. This circuit may be a coherent trigger-based signal combining in space. In some embodiments, the starting phase of the radiated pulse is a determined phase. Each transmitter may be equipped with a programmable delay that is used to calibrate the timing mismatch between the elements of a large array. In some embodiments, the system may radiate high-power pico-second pulses with a large array of coherent transmitter elements. In some embodiments, radar sensors provide an on-chip antenna. The on-chip antenna may be selected from, but is not limited to, a bow-tie, inverted cone, substrate-coupled, loop, dipole, patch, helix, or slot antenna. In some embodiments, the antennas may be bow-tie shaped slot antennas that are suitable for broadband radiation in silicon. FIGS. 2A-2D shows a broadband on-chip antenna 10 with its feed including (a) a close-up view of a bow-tie shaped antenna, (b) a view of the antenna on a substrate and lens, (c) a close-up view of the bow-tie shaped slot antenna with DC biasing pads and transmission lines, and (d) another view of the antenna on a substrate and lens. As shown in FIG. 2B, the bow-tie shaped antenna 10 may be formed on the surface of a substrate 20, such as by forming a metal in a bow-tie shape on a silicon substrate. A thin layer 15 may be formed between antenna 10 and substrate 20, such as a silicon oxide. A lens 30 may be provided on the back surface of the substrate, and the antenna 10 may be exposed to air 40. In another embodiment shown in FIG. 2C, antenna 10 may be coupled to transmission-lines (or t-lines) 50 for transmission and/or impulse matching. As a nonlimiting example, t-lines 50 may include a capacitor array utilized for impulse matching. The t-lines 50 may be coupled to DC pads 60. The antenna and feed shown is connected to a core circuit, which injects high power narrow pulses to the antenna by switching the current. The switching circuit may be based on switching an inductor's current to produce abrupt high voltages. A baseband generator can easily produce this trigger signal. FIG. 3 is an illustrative embodiment showing a block diagram of a picosecond pulse radiator 300. A trigger 310 may provide a digital rising-edge or falling-edge signal to a digital driver 320. Digital driver 320 may improve the strength of the signal provided to the switching circuit. Digital driver 320 may also reduce the rise or fall times of the digital signal. The switching circuit 330 may provide pulses to the antenna 340 by switching current. The switching circuit 330 may provide a fast switch that turns the current on or off. If the switch circuit 330 is on, the antenna 340 stores energy. When the switching circuit 330 is switched off, the antenna 340 releases the stored energy and radiates a short impulse.

In some embodiments, the radar sensor may provide an on-chip antenna that radiates from a planar back side. A bow-tie shaped slot antenna may be formed by depositing metal lines on the surface of a substrate. As shown in FIG. 2A, the bow-tie shaped antenna provides two approximately triangular shaped areas intersecting each other at points of the triangular shaped areas to form a mirror image. In some embodiments, the outer edges of a bow-tie shaped antenna may be curved to increase antenna bandwidth. The triangular areas represent regions where metal is absent, whereas the metal surrounds these regions. In other embodiments, the antenna may be formed between the substrate and a layer below the substrate. A ground shield is not utilized to aid radiating from the backside of the chip. A backside layer may be provided below the substrate. In some embodiments, the backside layer may have a dielectric constant that is much larger than the air. For example, as a nonlimiting example, the substrate may be Si ($\varepsilon=11.7$) versus air ($\varepsilon=1$). This may cause a planar substrate to convert the useful radiated power into undesired surface-waves. In this case, a hemispherical lens can be used in the back of the silicon substrate to minimize the surface waves. Further, an optional impedance matching layer may be provided to match the impedance of the silicon substrate to air or the drilling mud.

In some embodiments, an impulse radiator with a differential circuitry and electromagnetic structure may be implemented. As a nonlimiting embodiment, a differential inverted cone on-chip antenna may be used for impulse radiation, such as shown in FIGS. 19A-19D. An inverted cone antenna may provide an inverted cone shaped opening, which may also be characterized as a combined semicircle and triangle, in a metal layer. A smaller inverted cone shaped metal layer may be deposited in the opening. As shown, the inverted cone antenna is arranged so that the layers also form a mirror image with the pointed ends of the inverted cone facing away from each other. Such an antenna may provide a large bandwidth and consumes a small area. Due to the differential architecture of the impulse radiating circuit, two single-ended inverted cone antennas are used to form a differential antenna pair. A differential antenna provides higher efficiency by cancelling the substrate modes. In this design, biasing voltages can control the amplitude and sign of the radiated impulse. By optimizing the spacing between two elements of the differential antenna pair, the percentage of the power coupled to the substrate modes can be minimized. This results in a higher radiation efficiency. In addition to the spacing between the elements of the antenna pair, another factor that impacts the radiation efficiency is the substrate thickness. The substrate thickness may be carefully chosen to minimize the substrate modes.

In some embodiments, the solid-state radar sensor may be capable of operating in temperatures up to 300° C. or less. This is because the SiGe transistors have a current gain of larger than one in temperatures as high as 500° C.

In some embodiments, the solid-state radar sensor implemented with 130 nm Silicon-Germanium BiCMOS process technology. In some embodiments, the sensor may be a single-chip sensor. The sensor may include frequency generation blocks, transmitter, receiver, and integrated antennas. In some embodiments, all of these electronic circuitries may be integrated on a single-chip with area of 5 mm×5 mm or less. In some embodiments, all of these electronic circuitries may be integrated on a single-chip with volume of 5 mm×5 mm×0.3 mm or less. In some embodiments, all of these electronic circuitries may be integrated on a single-chip with a volume in the mm$^3$ range.

In an illustrative embodiment, an imaging system with at least one radar sensor transmits ultra-short time-domain impulses to a portion of a formation while positioned in a wellbore. In some embodiments, the impulses are in a frequency range equal to or between 1 GHz to 1 THz. The impulses may be transmitted to the formation at various vertical positions and azimuth angles, and time-domain signals may be measured at the various positions and angles. The vertical position and azimuth angles may be measured and recorded using any suitable downhole tools. These impulses are reflected back by the formation towards the imaging system, and detected by the receiver(s) of the at least one radar sensor. These reflected signals will arrive in different times at the receiver dependent on the different boundaries provided by the formation. This time difference allows us to generate 3D images of the formation. With the separation in time from the impulse to receiving the reflected signal, the complex permittivity of the formation can be measured. In some embodiments, some calibration may be required to minimize the errors due to mud and mud-cake. The radar sensor can be used to measure the size of the fractures in horizontal drilling.

The radar sensor can also be used to image the cross section of oil pipelines during production. The pipeline images provide useful information about the geometry of the pipeline, deposition thickness of asphaltenes and wax, velocity of the fluid, as well as size, type, concentration of gas bubbles, water, or solid particles in the flow, or combinations thereof.

Experimental Examples

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

Figure 4:
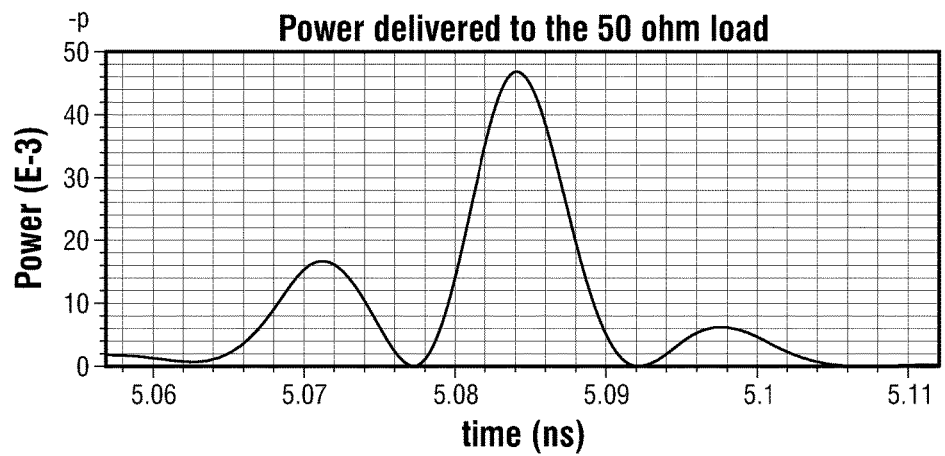
FIGS. 4 and 5 respectively show simulation results of the power (E-3) to 50Ω v. time (ns) and transient antenna voltage (V) v. time (ps)
Figure 5:
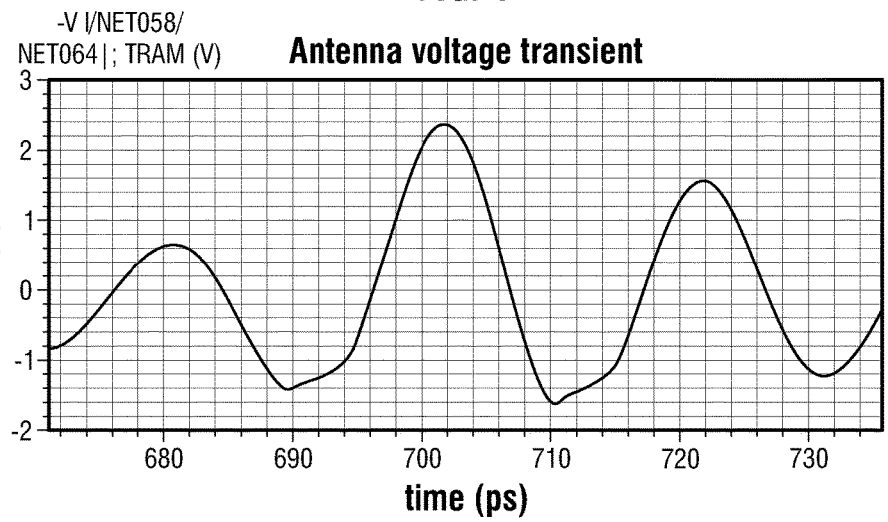
Figure 6A:
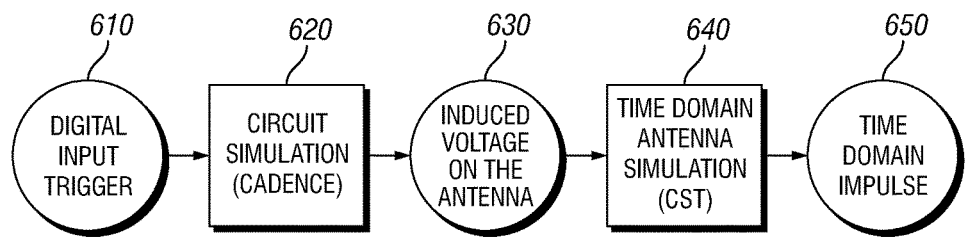
FIGS. 6A-6C show an electromagnetic simulation of the radiated signal, a corresponding color-map simulation, and far-field E-field v. time.
Figure 6B:
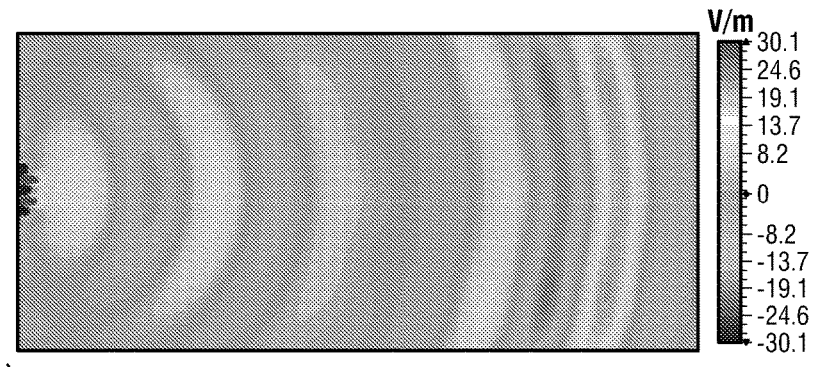
Figure 6C:
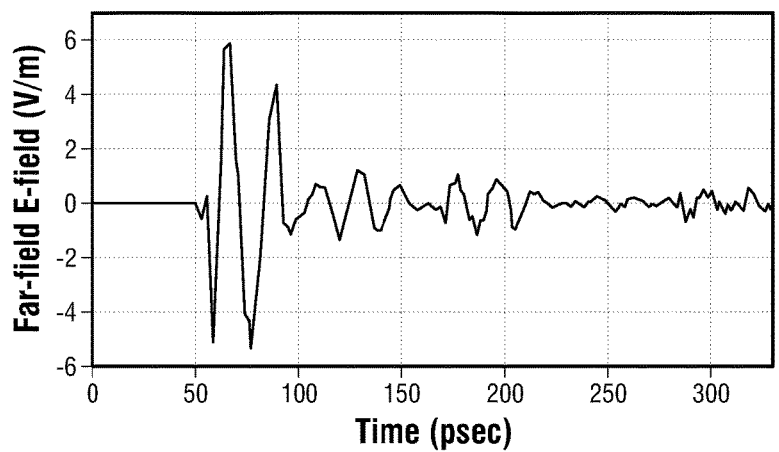
Figure 7:
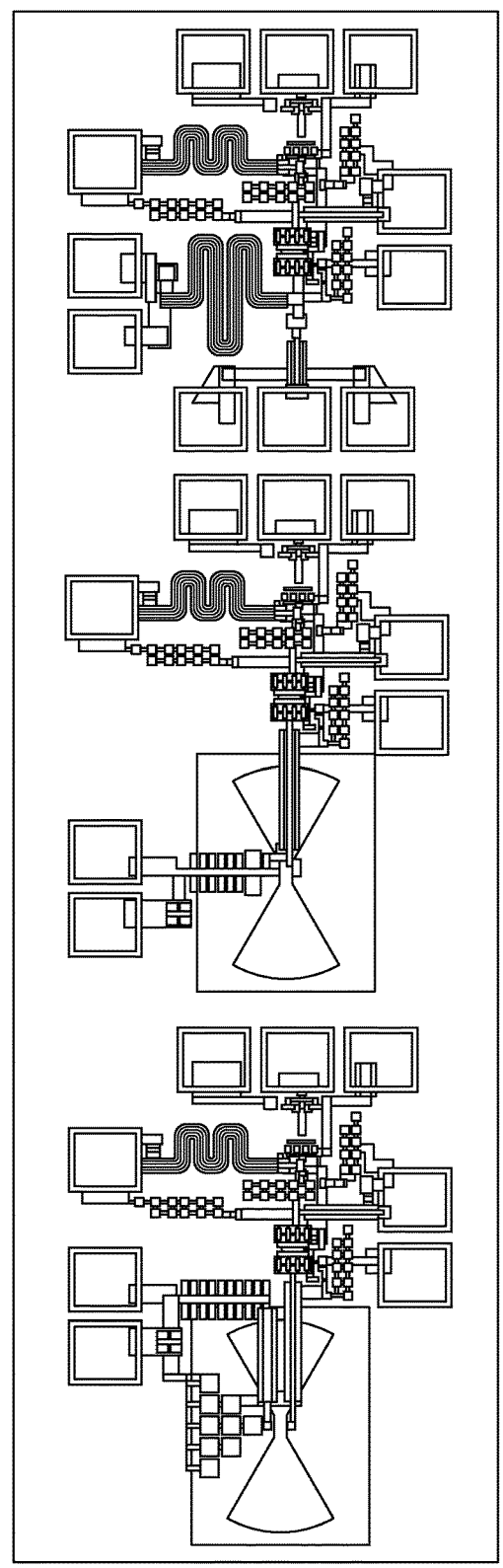
FIG. 7 is an illustrative embodiment of the layouts of three circuits.

Post-layout simulations of the core circuit along with electromagnetic simulations of the radiating structure illustrated that this impulse generation technique is suitable for high frequency radar signals due to the rapid on/off switching provided. Three nonlimiting versions of the circuit have being fabricated. Two of these impulse radiators have on-chip antennas and the third one delivers power to a 50Ω load. FIGS. 4 and 5 show the simulation results of the 50Ω and antenna versions. FIGS. 6A-6C show the electromagnetic simulation of the radiated signal. As shown in 6A, a digital input trigger 610 is provided to circuit simulation (cadence) 620, which induces voltage on the antenna 630. The time domain antenna simulation (CST) 640 then provides a time domain impulse 650. A corresponding color-map simulation is shown in FIG. 6B, and far-field E-field v. time is shown in FIG. 6C. FIG. 7 shows the layouts of these three circuits. This circuit was fabricated in a 45 nm CMOS SOI technology.

In contrast with other radiators that modulate a continuous wave (CW) oscillator to generate narrow pulses, the radiators discussed herein do not require an oscillator. Instead, a direct digital-to-impulse converter with a broadband on-chip antenna may be implemented that generate and radiate coherent impulses with ultra-short duration. In some embodiments, the impulse signal may have a duration of 50 psec or less. In some embodiments, the impulse signal may have a duration of 10 psec or less. In some embodiments, the radiators may provide peak equivalent or effective isotropically radiated power (EIRP) of 13 dBm or more. In some embodiments, the radiator may provide a repetition rate up of 10 GHz or more.

These results are based on direct time-domain measurements using a sampling oscilloscope. In addition to the time-domain measurements, the frequency spectrum of impulse train is measured up to 220 GHz. The radiated impulses can be locked to a digital trigger with timing jitter of 270 fsec or less. This low level of timing jitter and the direct digital-to-impulse architecture of the circuit make it possible to build a coherent sparse array of widely-spaced impulse-radiating chips with an effective aperture that is larger than the size of each individual on-chip antenna by several orders of magnitude. A large aperture is essential in generating images with high angular resolution. In order to demonstrate coherent spatial combining with widely-spaced elements, two impulse-radiating chips are placed with a spacing of 11 cm and their combined signal in the far-field is measured. This chip spacing can be as large as few meters or as small as 1 mm.

Figure 8A:
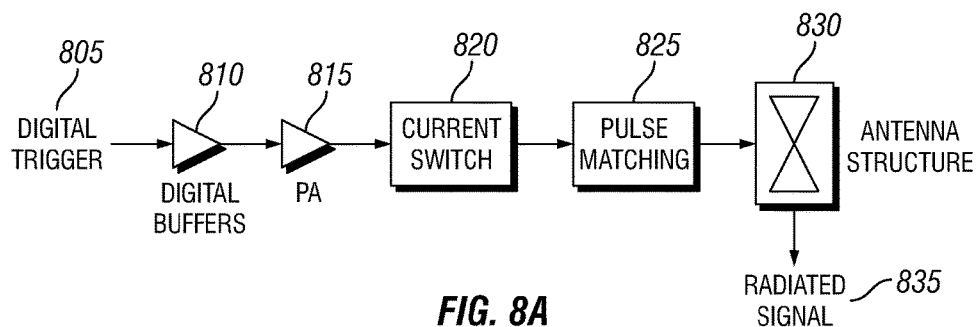
FIGS. 8A-8D are illustrative embodiments of a block diagram of the impulse radiator, digital trigger signal, radiated signal, and schematic of the digital-to-impulse radiator, respectively.
Figure 8B:
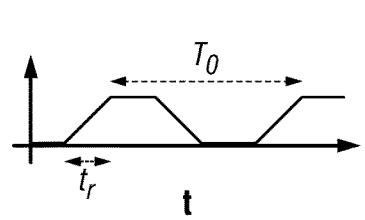
Figure 8C:
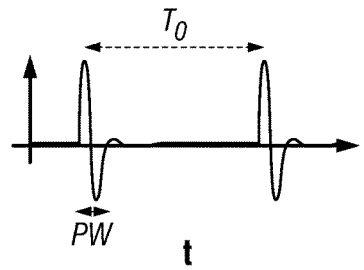
Figure 8D:
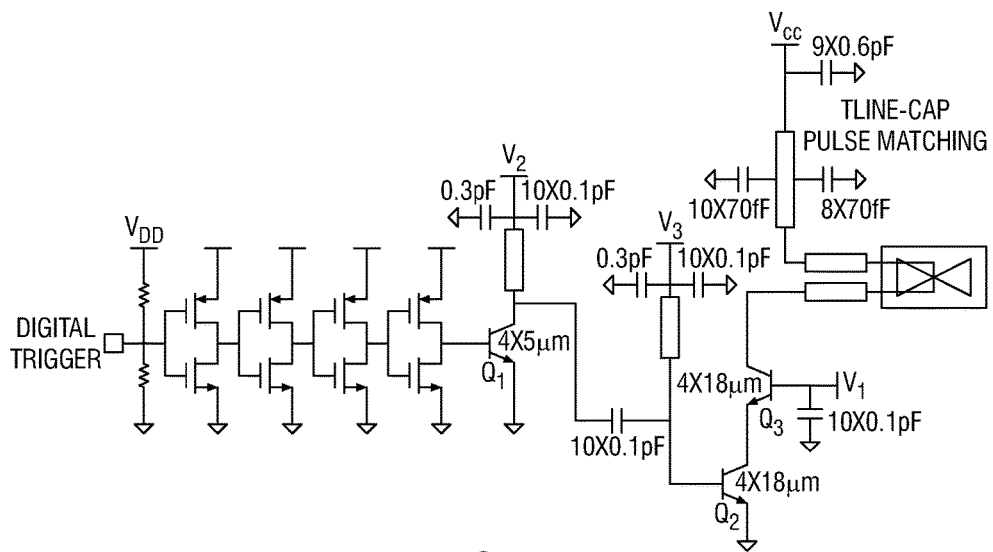
Figure 9A:
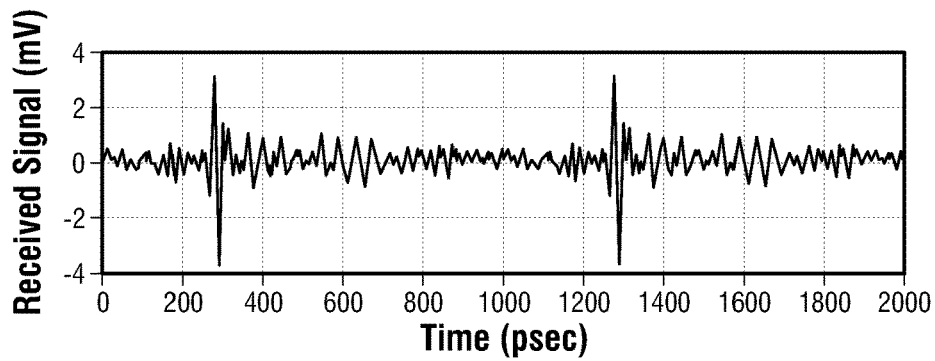
FIGS. 9A-9D show the measured time-domain results of the impulse-radiating chip (raw data) and spectrum of the EIRP.
Figure 9B:
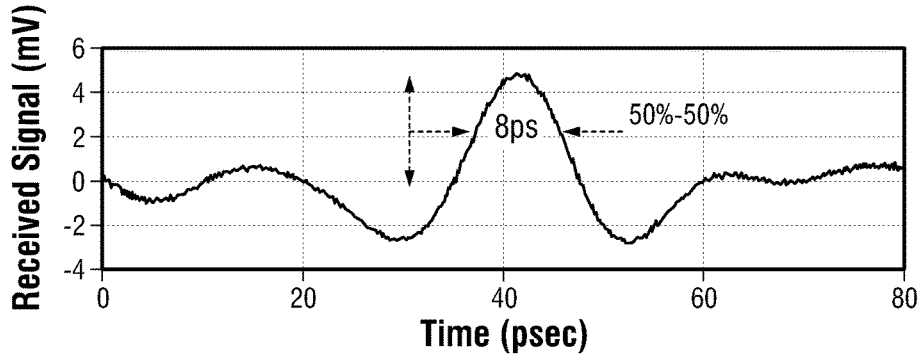
Figure 9C:
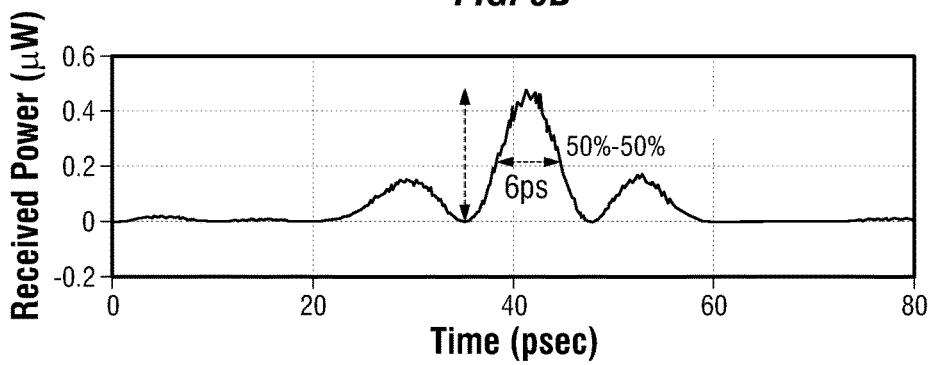
Figure 9D:
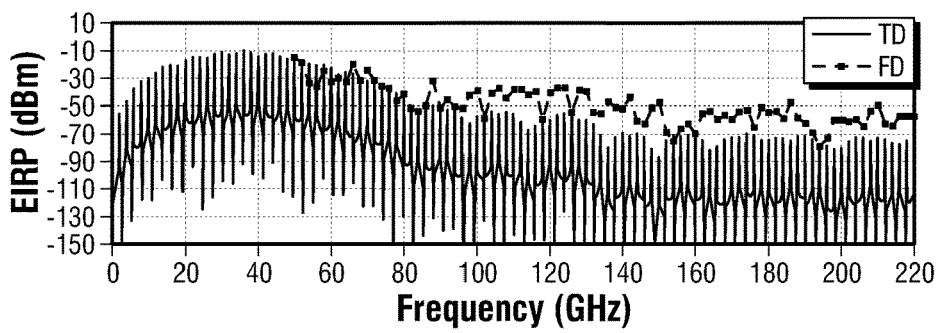

Illustrative embodiments of a block diagram of the impulse radiator, digital trigger signal, radiated signal, and schematic of the digital-to-impulse radiator are shown in FIGS. 8A-8D. As shown in FIG. 8A (and a more detailed schematic in FIG. 8D), a digital trigger 805 is coupled to digital buffer(s) 810, power amplifier (PA) 815, current switch 820, pulse matcher 825, antenna 830. Digital buffer(s) 810 may buffer the input (shown in FIG. 8B). A power amplifier (PA) 815 may increase the input and provide edge sharpening. The current switch 820 may provide a fast switch that allows the antenna 830 to store and release energy, thereby converting the input to a pulse. Pulse matching 825 may be utilized to reduce ringing, maximize an amplitude of the impulses, and/or minimize a pulse width of the impulses. The radiated signal 835 outputted by the antenna 830 is an impulse as shown in FIG. 8C. As a nonlimiting example, a digital trigger signal with a rise time of 120 psec is fed to the input of the chip. A series of digital buffers reduces the rise time of the signal to 30 psec and sends it to a power amplifier (PA) for further amplification. An antenna is designed to radiate ultra-short impulses. The on-chip antenna is connected to a switch. When the switch is on, the antenna is energized by storing a DC current. When the switch is turned off by the PA, the current stored in the antenna radiates ultra-short impulses that are coherent with the digital trigger. A transmission line based matching network is used to maximize the energy of each impulse while minimizing its duration.

The impulse radiator can operate in two modes. In the first mode, a positive impulse is radiated that is locked to the rising edge of the input trigger. In the second mode, a negative impulse is radiated, which is locked to the falling edge of the input trigger. Depending on the basing of node $V_3$, only one or both of these modes can be activated. In addition, the amplitude of the radiated impulses can be modulated by the voltage at node $V_2$ as shown.

A distributed network of bypass capacitors are used at the biasing points to ensure fast delivery of electrical charges to the base node of transistor $Q_3$. The edges of the slot bow-time antenna are curved to achieve a larger bandwidth. To minimize the substrate modes, increase the radiation efficiency, and minimize the ringing, the antenna may be coupled to a silicon lens with radius of 6 mm and extension length of 0.4 mm. The resistivity of the silicon lens is 10 KΩcm. The antenna may be implemented using a copper or aluminum layers. In this non-limiting example, copper metal was used. The matching transmission lines may be fabricated using copper and aluminum layers. In a non-limiting example of a bow-tie antenna (e.g. FIG. 2C), additional metal layers may be used to implement the transmission lines. In this process, some of the metals layer may be made of copper and some of the metal layers may be made of aluminum. The antenna may be coupled to the silicon lens through the substrate.

One of the main challenges in measuring a time-domain waveform of a short impulse is the receiving antenna of the measurement setup. The receiving antenna needs to have a constant group delay to prevent signal distortion. Although horn antennas have been used by others, due to the non-constant group delay of the horn antenna the received pulse becomes distorted. For the systems and methods discussed herein, a custom impulse antenna with flat gain and constant group delay may be used as the receiver. This receiving impulse antenna may be fabricated on a printed circuit board (PCB) with a dielectric constant of 2.4. Comparison of the time domain signal received by the custom receiving antenna and the horn antennas confirmed that the horn antennas should not be used in measuring ultra-short impulses. Horn antennas were only use to extract the frequency spectrum of the impulse train. FIGS. 9A-9D show the measured time-domain results of the impulse-radiating chip (raw data), where the PCB-based antenna is used as the receiver. In this measurement, the receiving antenna was directly connected to an Agilent 86118A sampling head and a mm-wave lens with focal point of 60 mm was used to focus the power to the PCB antenna. In order to calculate the peak EIRP, the mm-wave lens is removed from the setup and the loss of the cable/connector (~4 dB) is de-embedded. By using a center frequency of 50 GHz in the Friis formula, a peak EIRP of 13 dBm is calculated.

The time-domain radiation pattern of the impulse-radiating chip is measured. FIGS. 10A-10C show the time-domain waveform as a function of angle in the E-plane of the antenna, and the frequency-domain EIRP of the impulse radiating. In both E- and H-planes, it is confirmed that the waveform of the impulse is not distorted by changing the angle.

Figure 12A:
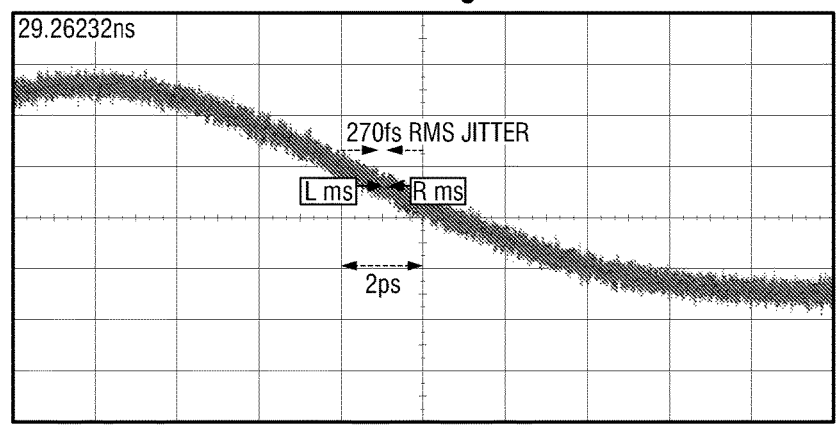
FIGS. 12A-12B show timing jitter of the combined signal and un-calibrated power spectrum.
Figure 12B:
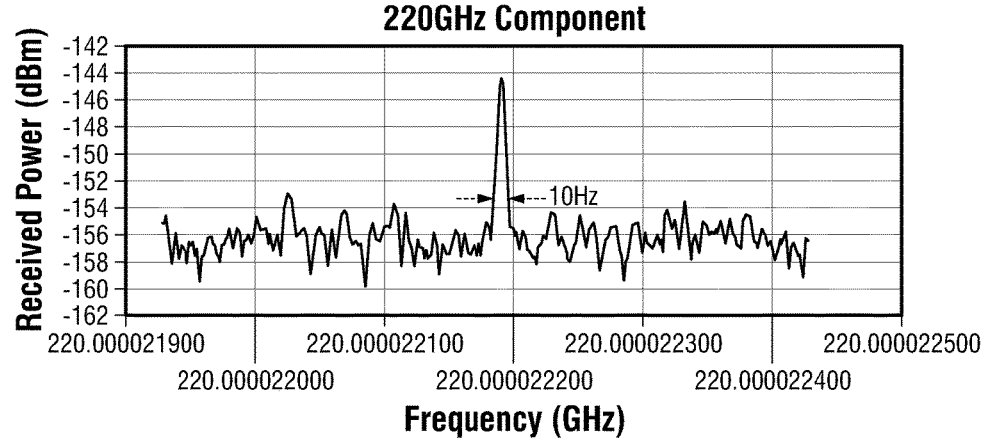

In addition to time-domain measurements, the frequency response of the impulse radiating chip is measured using an Agilent N9030A PXA Signal Analyzer, horn antennas, and OML harmonic mixers WR-15, WR-10, WR-08, and WR-05. The horn antennas and mixers cover the frequency range 50 GHz to 220 GHz. A distance of 370 mm between the impulse radiating chip and the horn antenna is chosen. In this measurement no focusing lens is used. In this measurement the loss of the mixer is de-embedded. The frequency spacing between the points in this diagram is equal to the repetition rate of 2 GHz. The radiation pattern of the impulse radiating chip at 70 GHz is reported in FIGS. 10A-10C. One of the unique features of the coherent impulse radiating chip is the high spectral purity of the radiated impulses. Based on the measured spectrum, 99% of the power of the 220 GHz tune is concentrated between frequencies 220,000,022,180 Hz and 220,000,022,190 Hz, which is only 10 Hz (FIGS. 12A-12B, and spectrum of the EIRP). This level of frequency stability is essential in performing high-resolution frequency-domain spectroscopy.

Figure 11A:
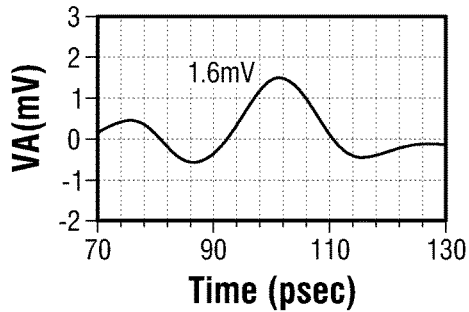
FIGS. 11A-11D respectively show the time-domain waveform of two impulse radiating chips, their combined signal, and set-up of the chips.
Figure 11B:
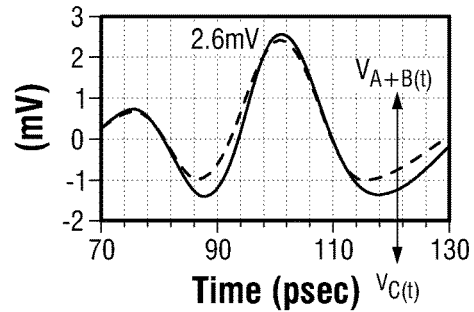
Figure 11C:
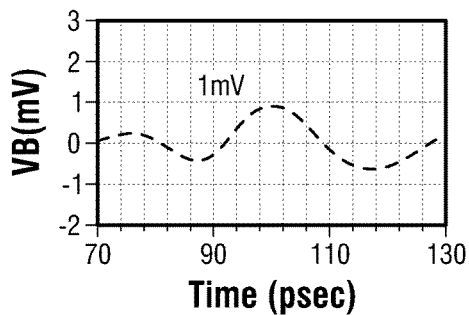
Figure 11D:
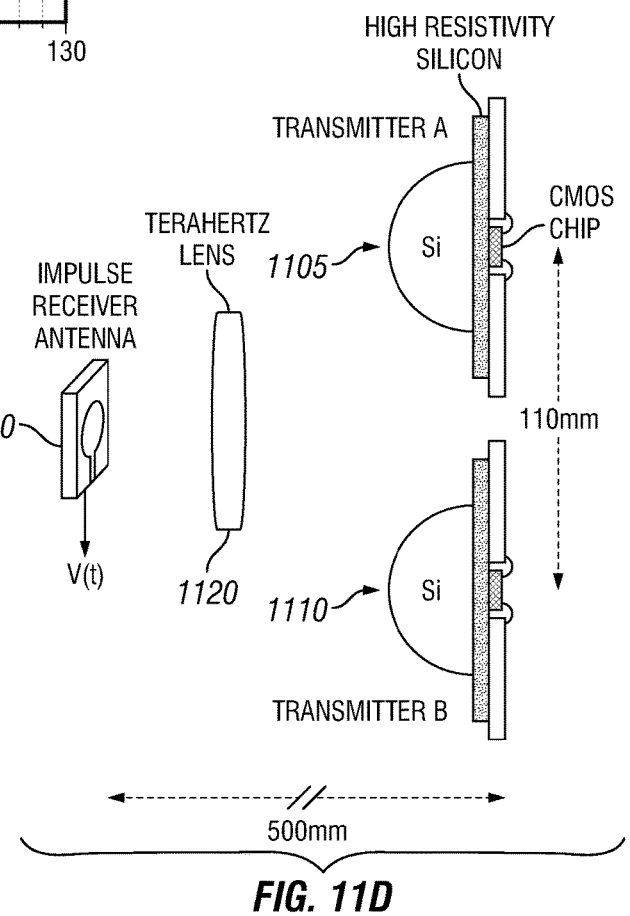

The precision synchronization of the digital trigger with the radiated impulses makes it possible to build a coherent sparse array with widely-spaced antennas to increase the effective aperture size. To demonstrate a coherent array, the radiated impulses from two separate chips are combined in the far-field. The digital trigger signal of each chip is provided by Tektronix Arbitrary Waveform Generator AWG7000. The AWG generates two synchronized trigger signals that can be shifted with respect to each other with a resolution of 1 ps. FIGS. 11A-11D show the time-domain waveform of two impulse radiating chips (FIGS. 11A & 11C), their combined signal (FIG. 11B), and set-up (FIG. 11D). Two transmitters, transmitter A 1105 and transmitter B 1110, were arranged with a separation of 110 mm. A lens 1120 and receiver antenna 1130 were positioned near the two transmitters. The timing jitter of the combined signal is calculated by the Agilent sampling oscilloscope 86100DCA and un-calibrated power spectrum around 220 GHz as shown in FIGS. 12A-12B. An RMS jitter of 270 fs is measured with an averaging of 64. The averaging is used to reduce the noise of the sampling head Agilent 86118A. The measured RMS jitter for averaging of 256 and 512 is 220 fs and 130 fs, respectively. This is the first coherent impulse-radiating array with widely-spaced antennas that can radiate sub-8 psec impulses. FIG. 13 shows a comparison of the specifications of the chip discussed herein with the other chips. The reported digital-to-impulse radiating chip is fabricated in IBM 0.13 μm SiGe BiCMOS process technology with $f_t$=200 GHz and $f_{max}$=270 GHz. A micrograph of the chip is shown in FIG. 14. The size of the chip including the on-chip antenna and the pads is 0.55 mm×0.85 mm.

Figure 15:
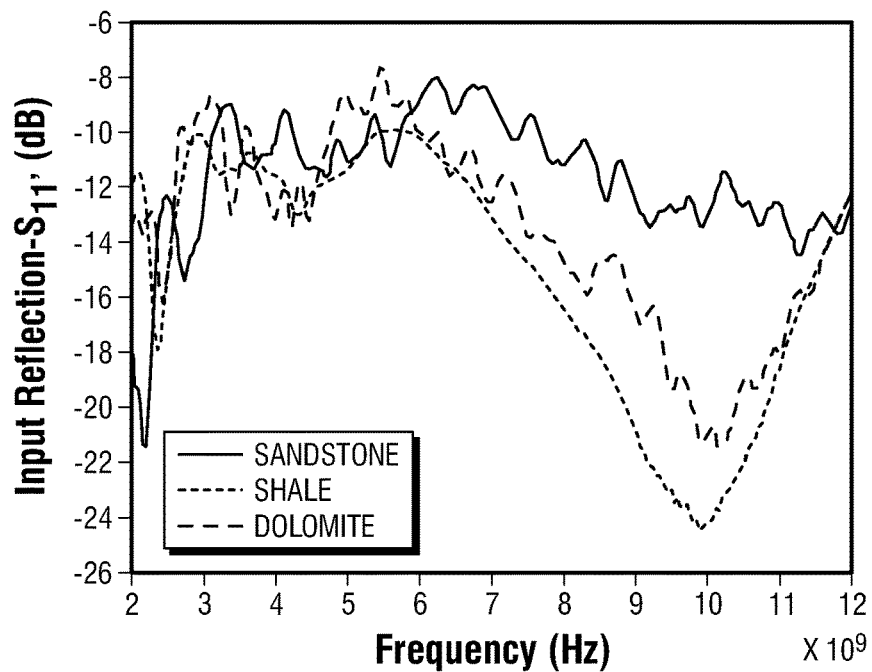
FIG. 15 shows input reflection results ($S_{11}$) in a frequency range.
Figure 16:
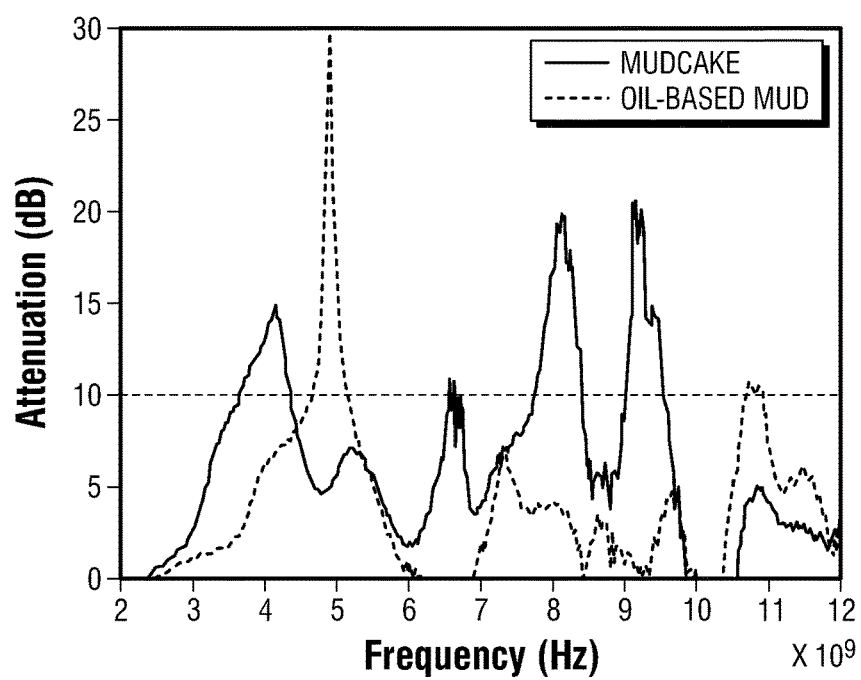
FIG. 16 shows attenuation of mudcake and mud for a frequency range.
Figure 17:
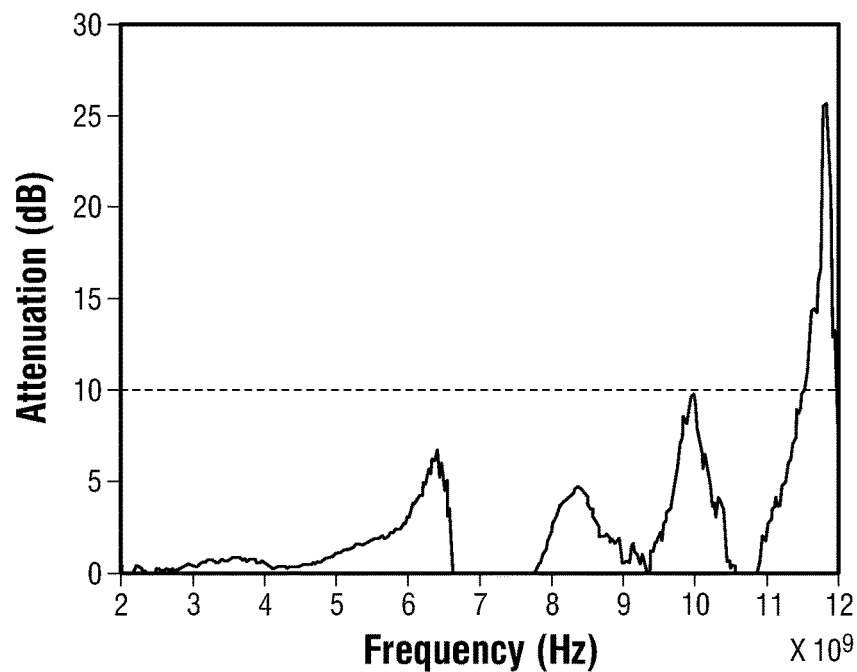
FIG. 17 shows the attenuation of fiberglass in a frequency range.
Figure 18:
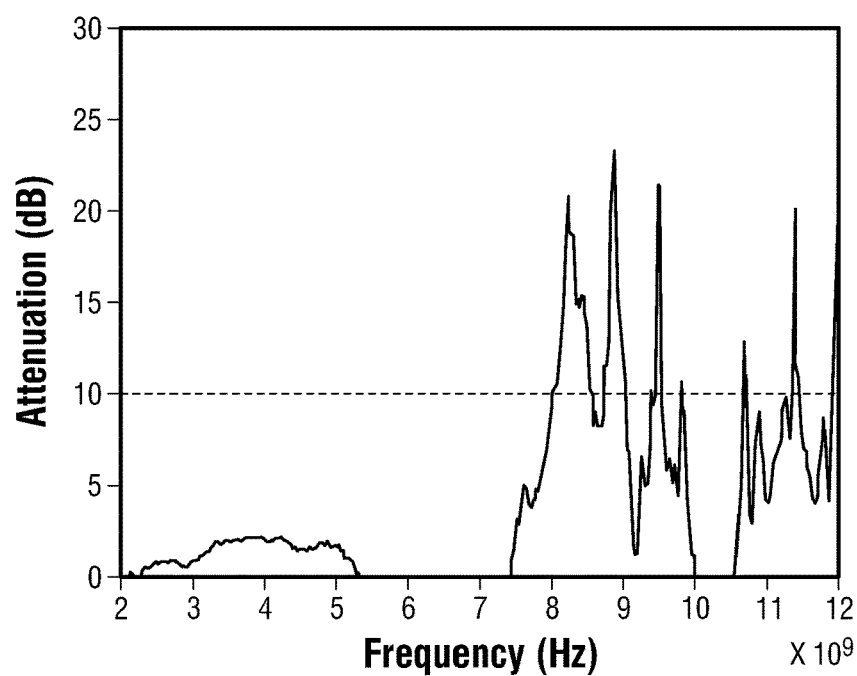
FIG. 18 shows the attenuation of PEK in a frequency range.
Figure 19B:
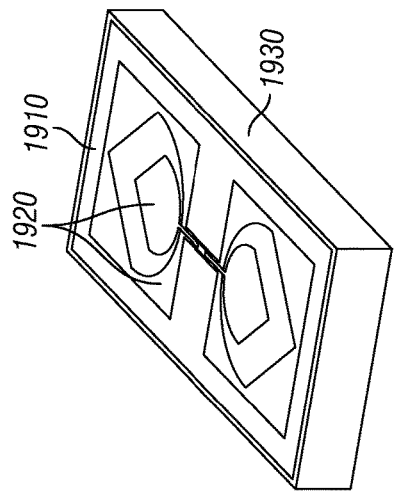
FIGS. 19A-19D is an illustrative embodiment of the differential inverted-cone on-chip impulse antenna, its assembly and design parameters from several views.
Figure 19D:
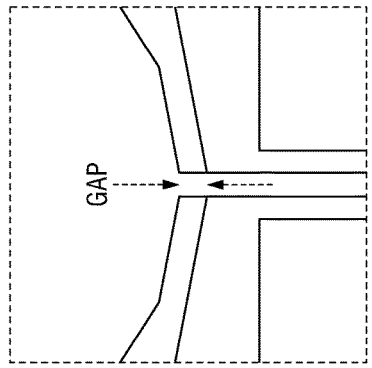
Figure 19A:
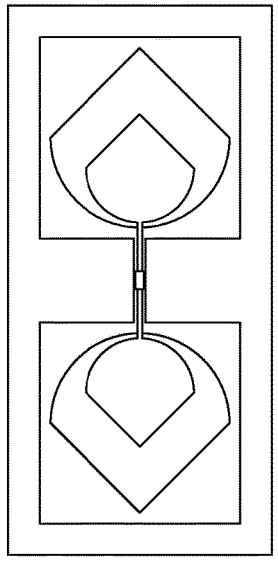
Figure 19C:
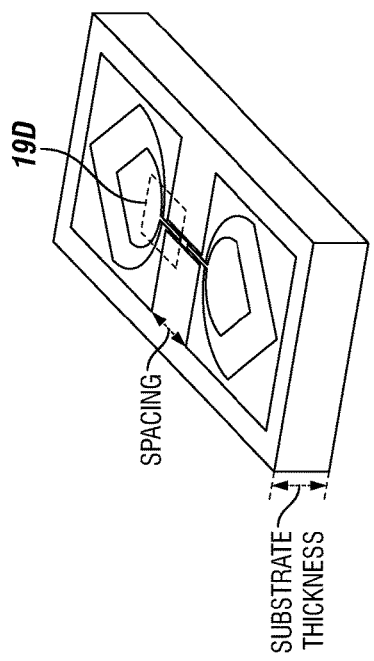

In yet another example, radar measurements of sandstone, shale, dolomite, mud-cake, and oil based mud are shown. FIG. 15 shows input reflection results ($S_{11}$) in a frequency range of 2-12 GHz. A significant difference between shale and sandstone in frequency range 6-12 GHz is observed. Shale behaves like a lossy (high absorption) material in frequency range 6-12 GHz. The radar sensor can easily distinguish between shale and sandstone. FIG. 16 shows attenuation of mudcake and mud for a frequency range of 2-12 GHz. The oil-based mud has a very sharp peak around 5 GHz. An attenuation of smaller than 10 dB can be easily calibrated by post-processing the measured data. As the result illustrate, mudcake and mud do not cause major problems in radar imaging. FIG. 17 shows the attenuation of fiberglass in a frequency range of 2-12 GHz. In a wide frequency range, the attenuation of fiberglass is negligible. FIG. 18 shows the attenuation of polyetherketone (PEK) in a frequency range of 2-12 GHz. In a wide frequency range, the attenuation of PEK is negligible. In frequencies higher than 8 GHz, several narrow-band resonances were observed. As such, it is clear that Fiberglass and PEK may be suitable for packaging sensors and protecting them from high-pressure. Additionally, any suitable material with negligible attenuation that can also withstand high pressure may be used for packaging sensor. From the experimental results shown, it is clear that the input reflection results can be utilized to detect different materials in high frequency ranges without significant attenuation.

Figure 22A:
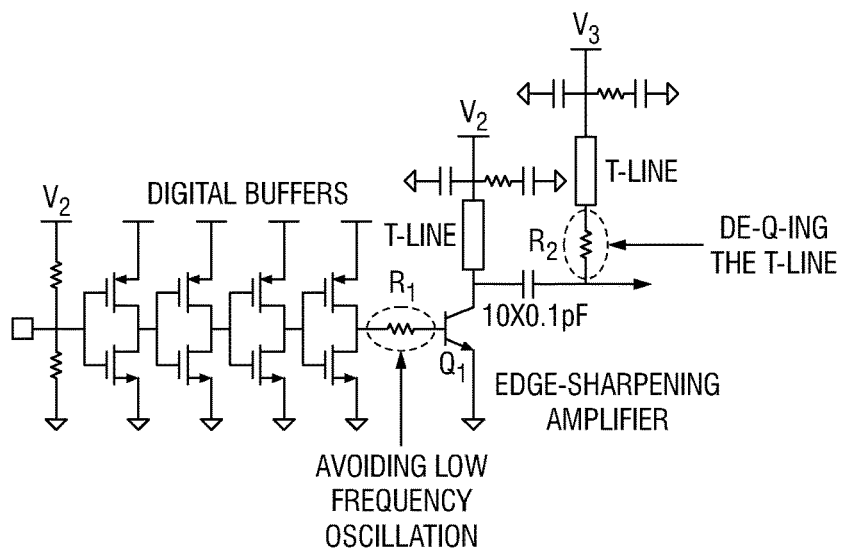
FIGS. 22A-22B show schematics of an impulse radiator circuit.
Figure 22B:
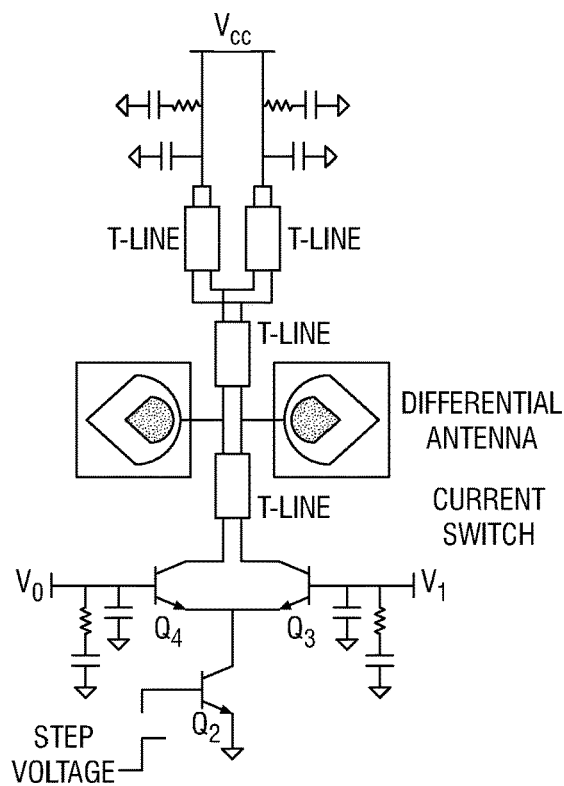
Figure 23A:
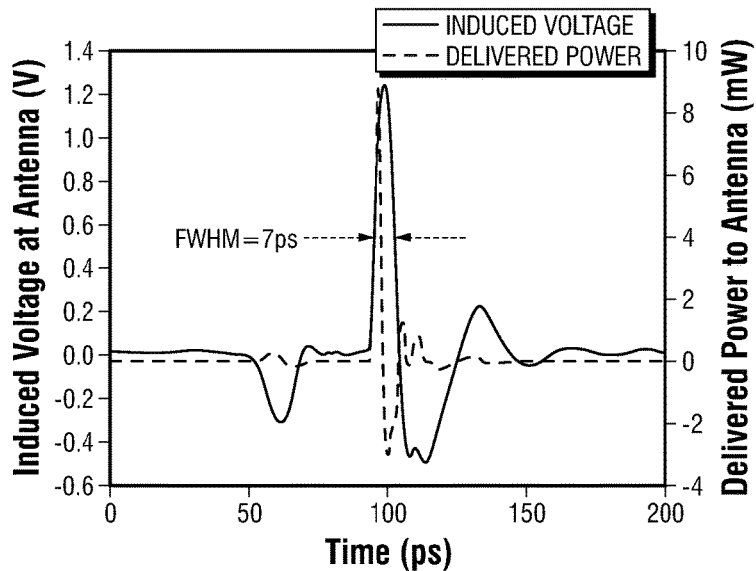
FIGS. 23A-23B show circuit simulation results and electromagnetic simulation results of the differential impulse radiator.
Figure 23B:
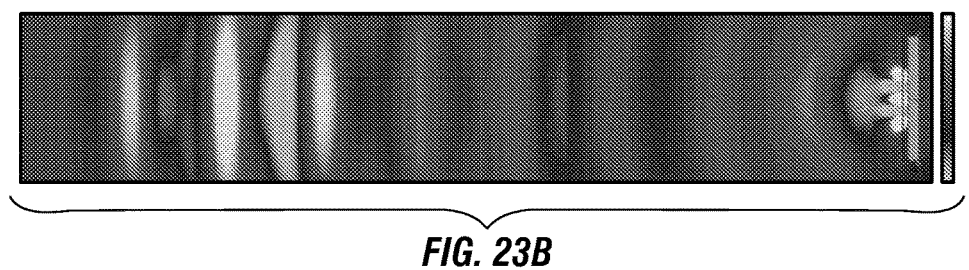

A differential pair of bipolar transistors and a transistor as the current source make the current-switch stage. The load of this stage is the antenna with the impulse matching network shown in FIGS. 19A-19D. An inverted cone antenna may include a first metal layer 1920 may be deposited on a substrate 1920. The first metal layer 1920 may form two approximately square shaped regions, each with openings in the shape on an inverted cone. A second metal layer 1920 may be formed in the shape of an inverted cone that is smaller than the aforementioned openings. The second metal layer 1920 may be deposited so that the smaller inverted cone is positioned within the aforementioned openings and a thin strip of the second metal layer is on top of the first metal layer. Further, an oxide 1910 may coat the top antenna. FIG. 20 shows the real and imaginary parts of the antenna impedance. FIG. 21 shows the architecture of this chip. As shown, a differential step current 2110 is provided to a pulse matcher 2120 that feeds antenna 2130. As discussed previously, the pulse matching reduces ringing. FIGS. 22A-22B show a detailed circuit schematics of the impulse radiator circuit. The bases of the differential transistor pair are biased at $V_0$ and $V_1$ voltages. A distributed network of bypass capacitors is used at the biasing points to ensure fast delivery of electrical charges to the base node of transistors $Q_3$ and $Q_4$. Due to the asymmetric biases on $Q_3$ and $Q_4$, the pair generates a non-zero differential current when the tail current source turns on. This current is fed through the impulse matching network and the antenna and causes impulse radiation. One of the unique features of this design is that voltages $V_0$ and $V_1$ can control the amplitude and sign of the radiated impulse. For $V_0 > V_1$, a positive impulse is radiated, while for $V_1 > V_0$, a negative impulse is radiated. The amplitude of the impulse is also set by the difference between $V_0$ and $V_1$. FIGS. 23A-23B show the circuit's electromagnetic simulation results.

Figure 24:
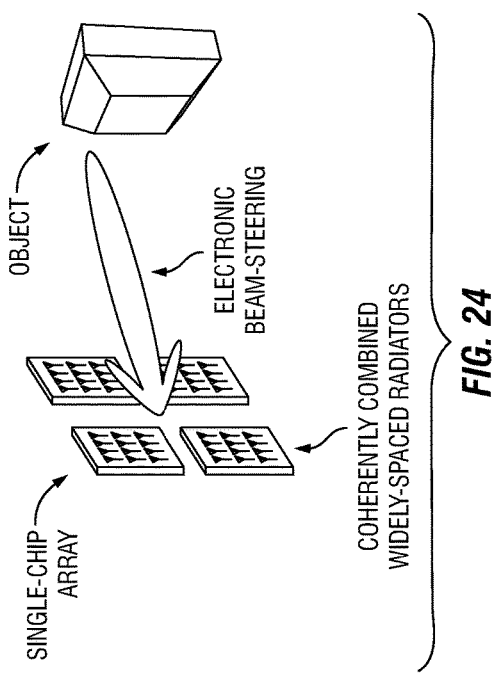
FIG. 24 is a schematic coherently combined widely space radiators.

FIG. 24 is a schematic coherently combined widely space radiators. A single-chip array may provide multiple antennas or radar sensors. Multiple single-chip arrays may be arranged near each other. With multiple single-chip arrays, electronic beam steering may be utilized.

Figure 25B:
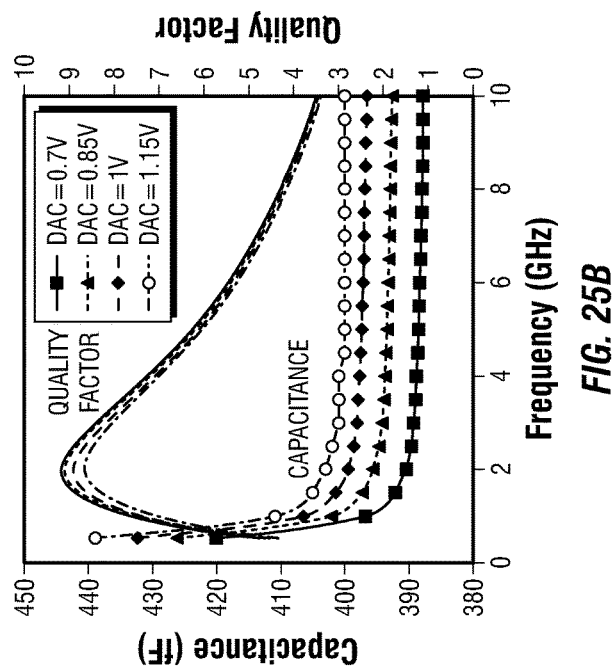
FIGS. 25A-25B are a schematic of the delay line and simulation results.
Figure 25A:
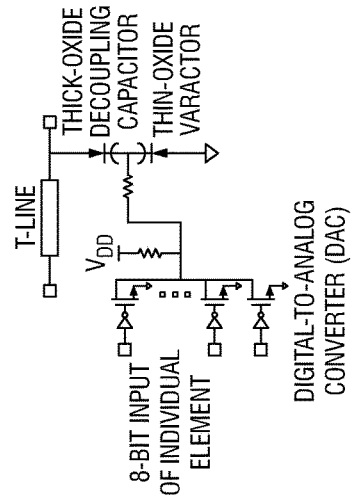
Figure 26A:
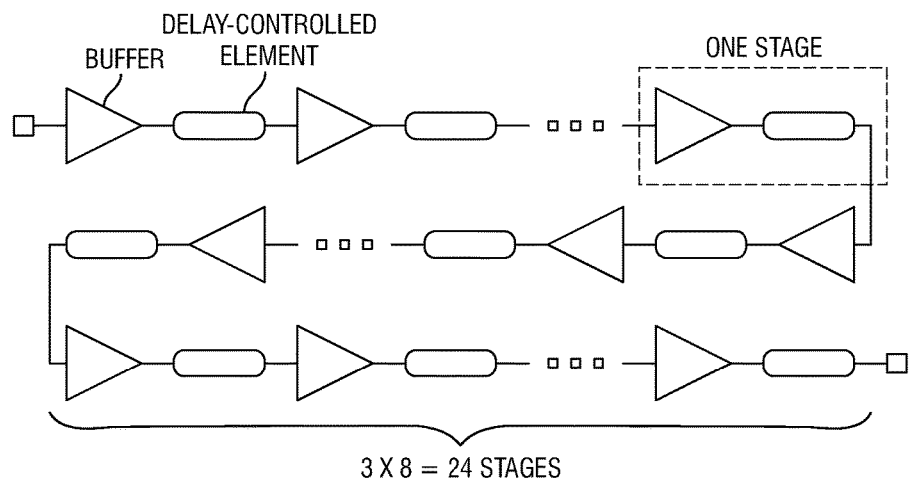
FIGS. 26A-26B shows the architecture and the chip micrograph for the delay line.
Figure 26B:
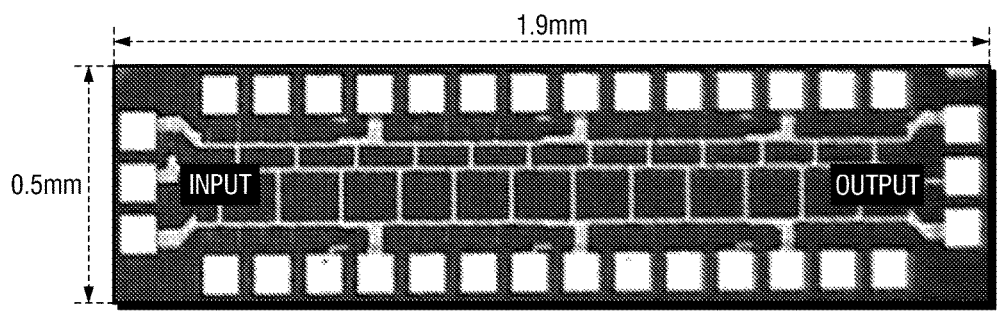

In this work, a programmable digital delay line is implemented which controls the timing delay of the input trigger to the impulse radiator. The delay line has total number of 16-bit inputs. Due to the need for high dynamic range of delay, 24 elements are cascaded which the delay of each individual stage is controlled by an on-chip digital-to-analog converter (DAC). Individual delay elements are in series with buffer stages (e.g. FIG. 26A). Each individual delay element may include a transmission line with six varactor loading. The analog output voltages of on-chip DACs control the capacitance of the varactors. This design compared to digital delay lines based on the change in the VDD of several buffer stages, has much lower power consumption due to almost zero DC current needed for varactors to change AC capacitance. FIGS. 25A-25B show the delay line circuit and simulations. FIGS. 26A-26B show the architecture and chip micrograph of the delay line.

Figure 28A:
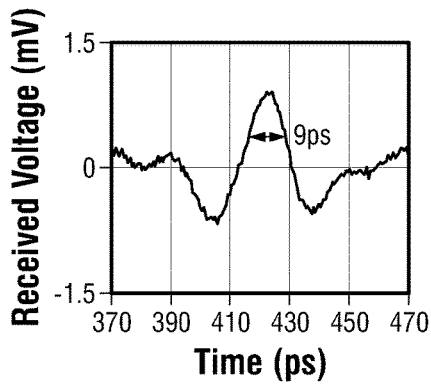
FIGS. 28A-28C show the measured time-domain results of the differential impulse-radiating chip (raw data)
Figure 28B:
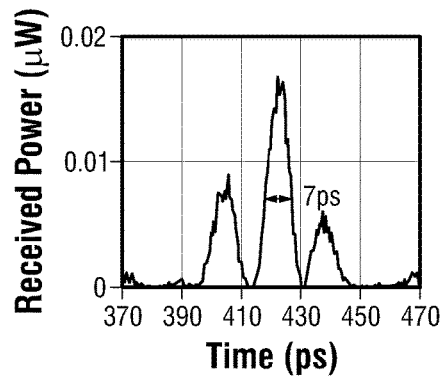
Figure 28C:
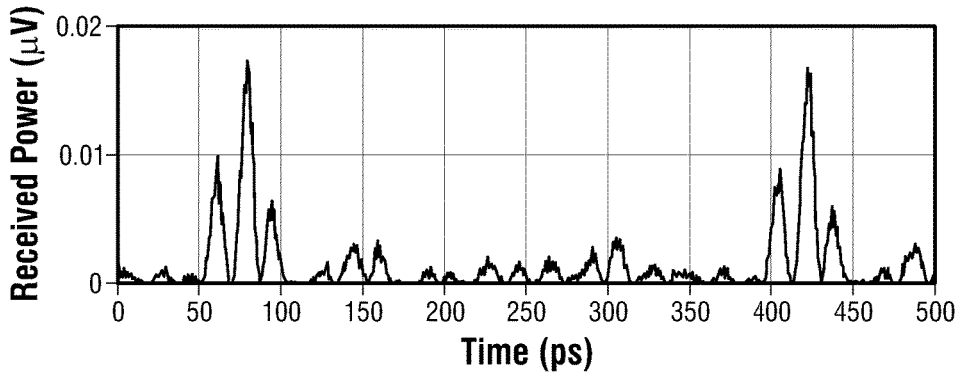
Figure 29A:
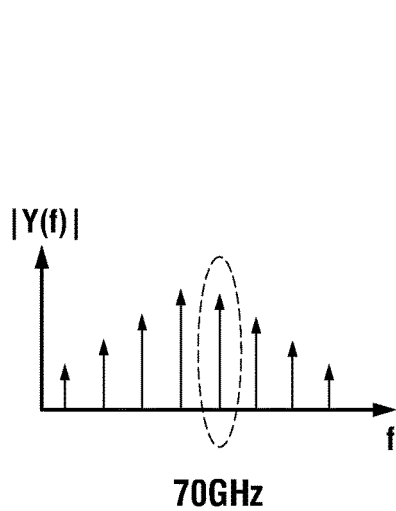
FIGS. 29A-29B show the picked frequency of 70 GHz and radiation pattern at this frequency.
Figure 29B:
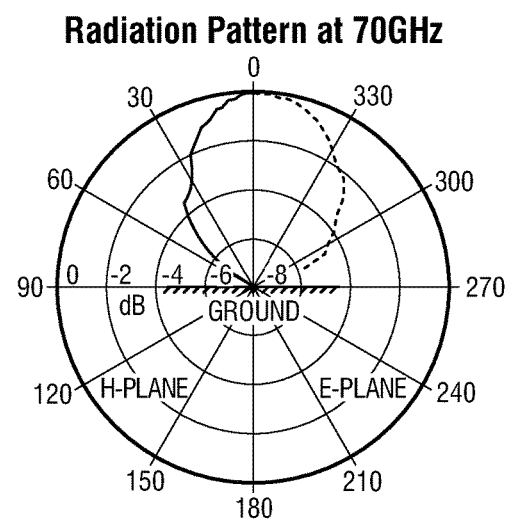
Figure 30A:
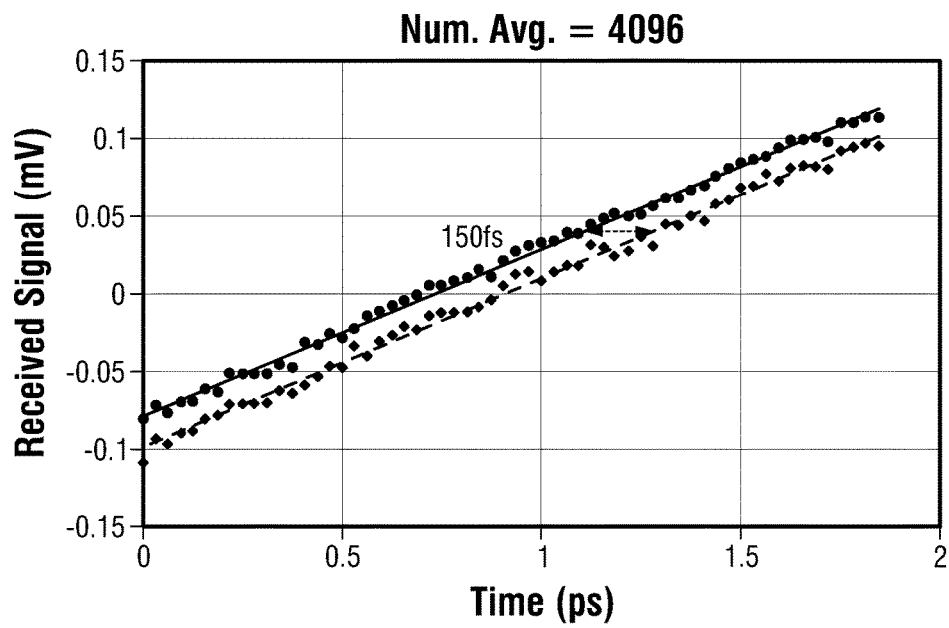
Figure 30B:
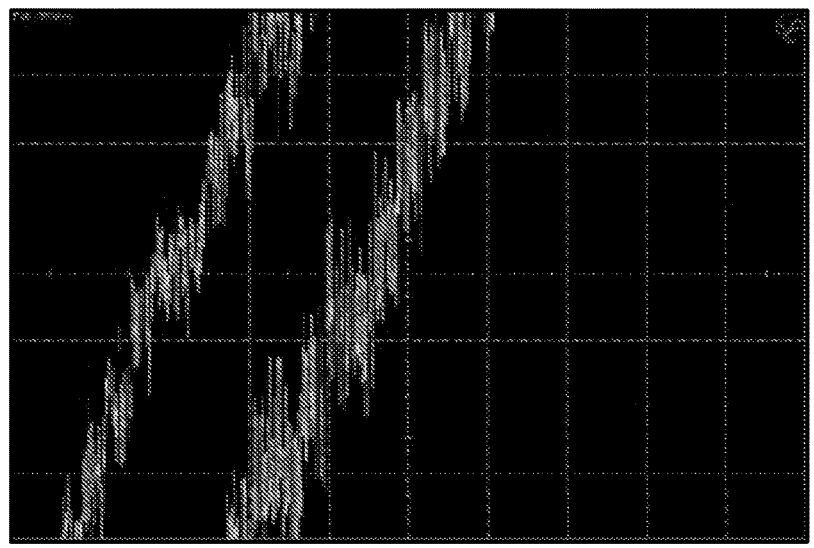

FIGS. 27A-27C show an illustrative embodiment of the measurement setup along with photographs of the front and back of the deigned impulse receiver antenna. FIGS. 28A-28C show the time-domain waveforms of the measured impulses from the differential impulse radiator chip. FIGS. 29A-29B show the picked frequency of 70 GHz and the radiation pattern. FIGS. 30A-30C show the delayed radiated impulses in the air and jitter measurements. FIG. 31 compares this chip with other impulse radiating chips.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A radar system comprising:
a digital trigger providing a digital signal, wherein the radar system is oscillatorless;
a switching circuit coupled to the digital trigger, wherein the switching circuit converts the digital signal to impulses;
an antenna coupled to the switching circuit, wherein the antenna converts the impulses to radiated impulse waves, and the antenna operates at a frequency of 1 GHz or greater; and
wherein the digital trigger, switching circuit, and antenna are integrated on a single chip.

2. The system of claim 1, further comprising a digital driver coupled to the digital trigger and switching circuit, wherein the digital driver reduces the rise or fall times of the digital signal.

3. The system of claim 1, further comprising a pulse matcher coupled to the current switch and the antenna, wherein the pulse matcher reduces ringing, maximizes an amplitude of the impulses, or minimizes a pulse width of the impulses.

4. The system of claim 1, wherein the radiated impulse waves have a duration of 50 psec or less.

5. The system of claim 1, wherein the single chip has an area of 5 mm×5 mm or less.

6. The system of claim 1, wherein the radiated impulse waves from the antenna can be focused into a spot size of 10 mm or less.

7. The system of claim 1, wherein the radar system provides active cancellation to prevent an output of a transmitter from coupling to an input of a receiver.

8. The system of claim 1, wherein the antenna is a bow-tie shaped slot antenna, inverted-cone shaped antenna, a substrate-coupled antenna, loop antenna, dipole antenna, patch antenna, bow-tie antenna, helix antenna, or slot antenna.

9. The system of claim 1, wherein the antenna does not have a lens.

10. A method for imaging with a radar sensor, the method comprising:
positioning a radar sensor near a pipeline or wellbore, wherein the radar sensor comprises
a digital trigger capable of providing a digital signal, wherein the radar sensor is oscillatorless,
a switching circuit coupled to the digital trigger, and
an antenna coupled to the switching circuit, wherein the digital trigger, switching circuit, and antenna are integrated on a single chip;
generating the digital signal with the digital trigger, wherein the digital signal is provided to the switching circuit;
converting the digital signal to impulses with the switching circuit; and
converting the impulses from the switching circuit to radiated impulse waves with the antenna, wherein the antenna operates at a frequency of 1 GHz or greater.

11. The method of claim 10 further comprises reducing ringing, maximizing an amplitude, or minimizing a pulse width of the impulses.

12. The method of claim 10, wherein the radiated impulse waves have a duration of 50 psec or less.

13. The method of claim 10, wherein the single chip has an area of 5 mm×5 mm or less.

14. The method of claim 10, wherein the radiated impulse waves from the antenna can be focused into a spot size of 10 mm or less.

15. The method of claim 10 further comprises providing active cancellation to prevent an output of a transmitter from coupling to an input of a receiver.

16. The method of claim 10, wherein the antenna is a bow-tie shaped antenna, inverted-cone shaped antenna, a substrate-coupled antenna, loop antenna, dipole antenna, patch antenna, bow-tie antenna, helix antenna, or slot antenna.

17. The method of claim 10, wherein the antenna does not have a lens.

18. The method of claim 10 further comprises:
receiving a reflected signal from a material with the antenna, wherein the radar sensor determines a time delay between transmittal of the radiated impulse wave and receipt of the reflected signal;
determining a frequency spectrum of the reflected signal, wherein the material and electrical permittivity of the material is determined by the frequency spectrum; and
determining a time-domain waveform of the reflect signal, wherein the material and electrical permittivity of the material is determined by the time-domain waveform.

19. The method of claim 18 further comprises determining a size of fractures from the reflected signals.

* * * * *